United States Patent
Hsiao et al.

(10) Patent No.: US 9,539,275 B2
(45) Date of Patent: Jan. 10, 2017

(54) MELANOGENESIS EFFECT OF SAPONINS OF GYNOSTEMMA PENTAPHYLLUM

(71) Applicant: Hong Kong Baptist University, Hong Kong (HK)

(72) Inventors: Wen Luan Wendy Hsiao, Hong Kong (HK); Ting Fung Tsang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 145 days.

(21) Appl. No.: 14/165,560

(22) Filed: Jan. 27, 2014

(65) Prior Publication Data

US 2015/0209376 A1 Jul. 30, 2015

(51) Int. Cl.
*C07H 15/256* (2006.01)
*A61K 31/704* (2006.01)
*A61K 31/706* (2006.01)
*A61K 36/424* (2006.01)
*A61K 31/00* (2006.01)

(52) U.S. Cl.
CPC ............ *A61K 31/706* (2013.01); *A61K 31/00* (2013.01); *A61K 31/704* (2013.01); *A61K 36/424* (2013.01); *C07H 15/256* (2013.01)

(58) Field of Classification Search
None
See application file for complete search history.

(56) References Cited

U.S. PATENT DOCUMENTS 6,423,323 B2 * 7/2002 Neubourg ............... 424/401

FOREIGN PATENT DOCUMENTS

JP S61-050907 * 3/1986 ............ A61K 7/00

OTHER PUBLICATIONS

English translation of abstract of S61-050907 above (1986) from Chemical Abstracts Service database CAPLUS.*
Englis machine translation of Japanese patent S61-050907 (Yuchi, Shigeru) published Mar. 1986, downloaded from https://www.j-platpat.inpit.go.jp/web/all/top/BTmTopEnglishPage.*
Lee et al., "Inhibition of melanogenesis and melanin transportation by Gynostemma pentaphyllum" Korean Journal of CHemical Engineering (2007) vol. 24 No. 4 pp. 655-659.*
William C.S.Tai et. at., Abstract of "Isolation of active ingredients with anti-cancer activity of total triterpenoids saponins of Gynostemma pentaphyllum by cell-based co-culture activity-guided fractionation assay", Center for Cancer and Inflammation Research, School of Chinese Medicine, Hong Kong Baptist University, 2010.
Chun-Ching Linet al., "Antioxidant and hepatoprotective effects of Anoectochilus formosanus and Gynostemma pentaphyllum", American Journal of Chinese Medicine, 2000, 28(1), p. 87-96.
Zhou Zengtong et. al., "Effect of gynostemma pentaphyllum mak on carcinomatous conversions of golden hamster cheek pouches induced by dimethylbenzanthracene: a histological study", Chinese Medical Journal, 1998, 111( 9 ), p. 847-850.
Jung-Chou Chen et. al., "Gypenoside induces apoptosis in human Hep3B and HA22T tumour cells", Cytobios, 1999, 100(393), p. 37-48.
Qwa-Fun Wang et. al., "Regulation of Bcl-2 family molecules and activation of caspase cascade involved in gypenosides-induced apoptosis in human hepatoma cells", Cancer Letters, 2002, 183(2), p. 169-178.
Ma Zhiru et. al., "Scavenging effects of Astragalus and Gynostemma pentaphyllum with its product on O2-. and .OH", Journal of Chinese Medicinal Materials, 1999, 22(6), p. 303-306.
Yan Ye et. al., "Screening of Chinese herbal medicines for antityrosinase activity in a cell free system and B16 cells", Journal of Ethnopharmacology, 2010, 129(3), p. 387-390.

* cited by examiner

*Primary Examiner* — Eric Olson
(74) *Attorney, Agent, or Firm* — Spruson & Ferguson (Hong Kong) Limited; Sam T. Yip

(57) ABSTRACT

The present invention provides composition and method for inducing melanogenesis. The composition comprising an effective amount of saponins extracted from herbal plants.

7 Claims, 21 Drawing Sheets

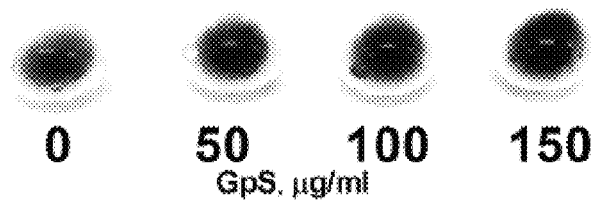
FIG. 3A
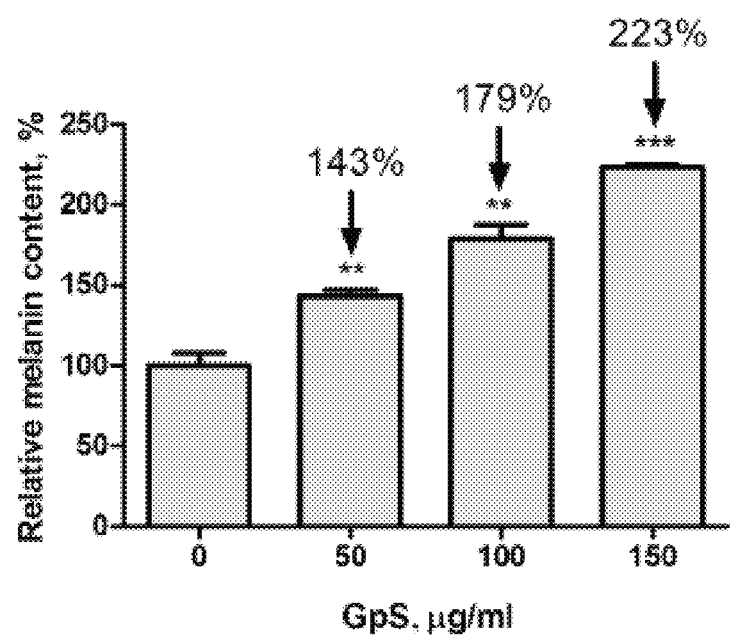
FIG. 3B
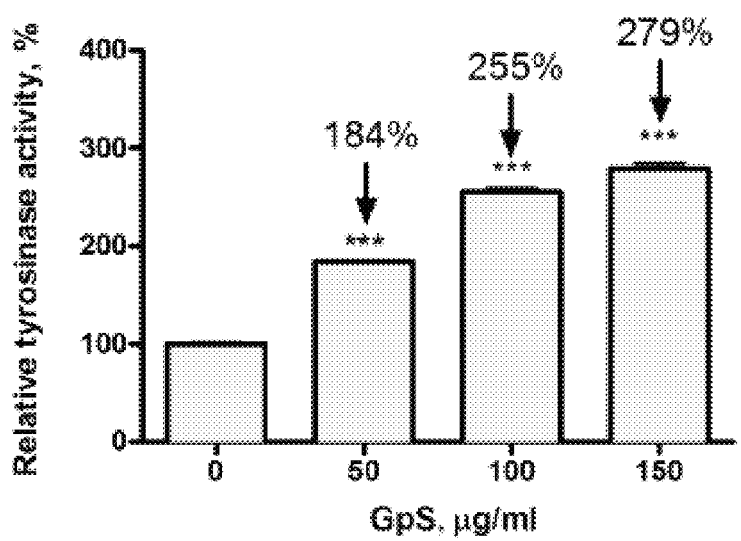
FIG. 3C
FIG. 3

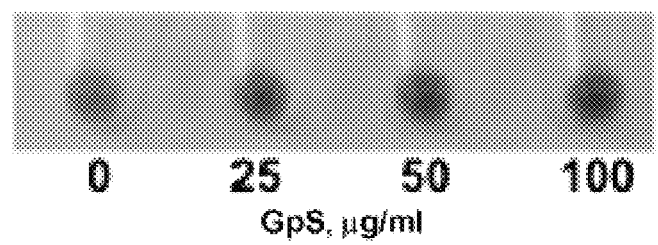
FIG. 4A
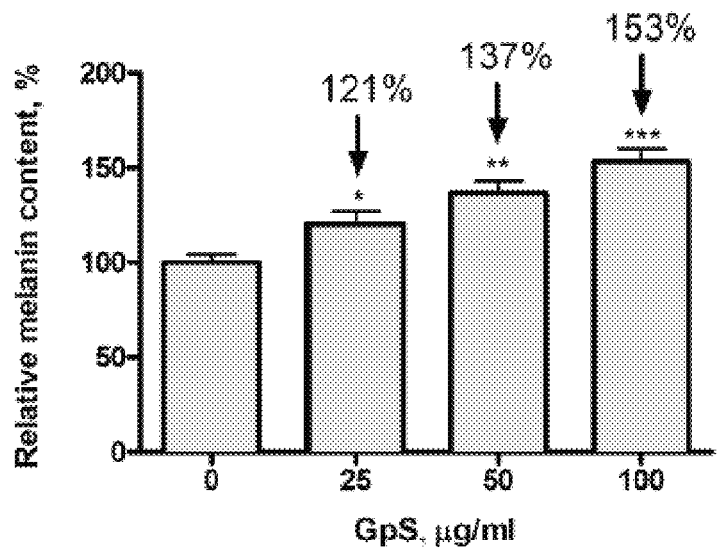
FIG. 4B
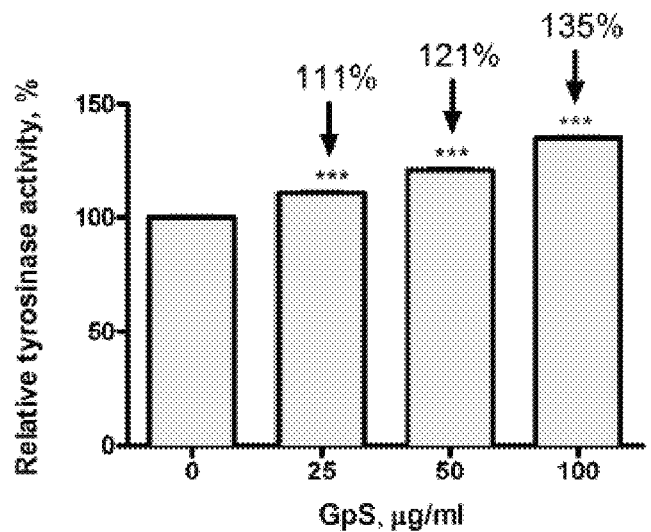
FIG. 4C
FIG. 4

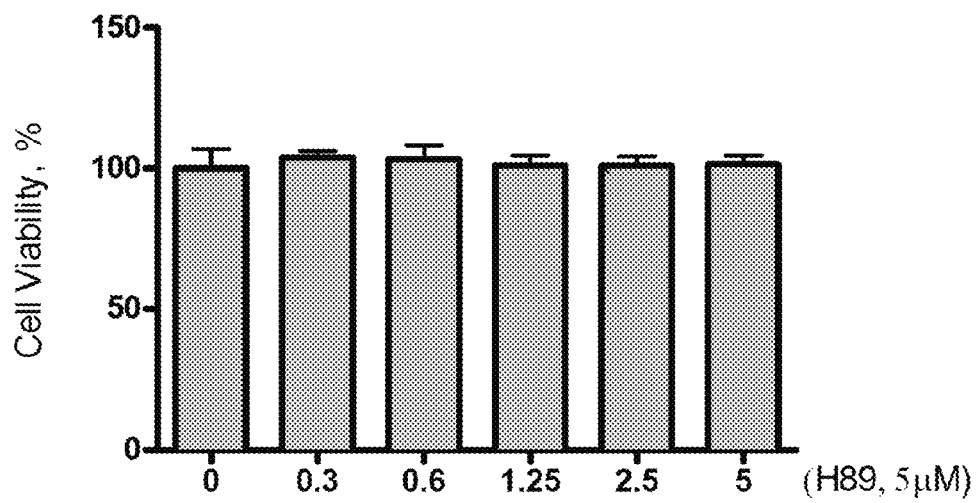
FIG. 7A
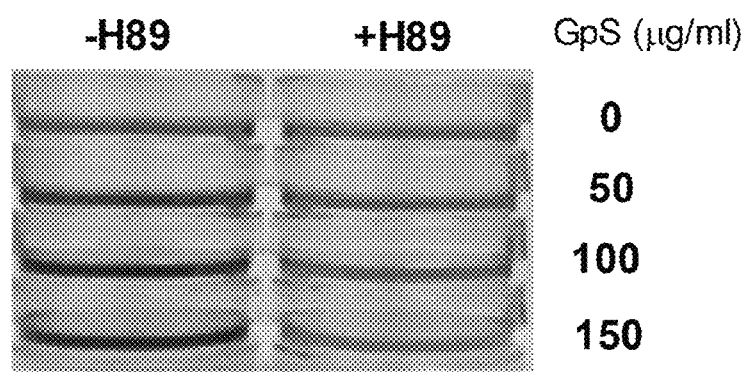
FIG. 7B
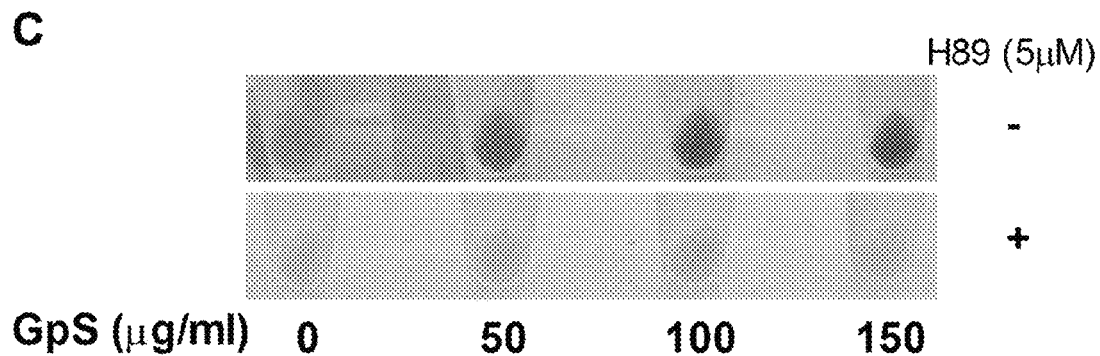
FIG. 7C
FIG. 7

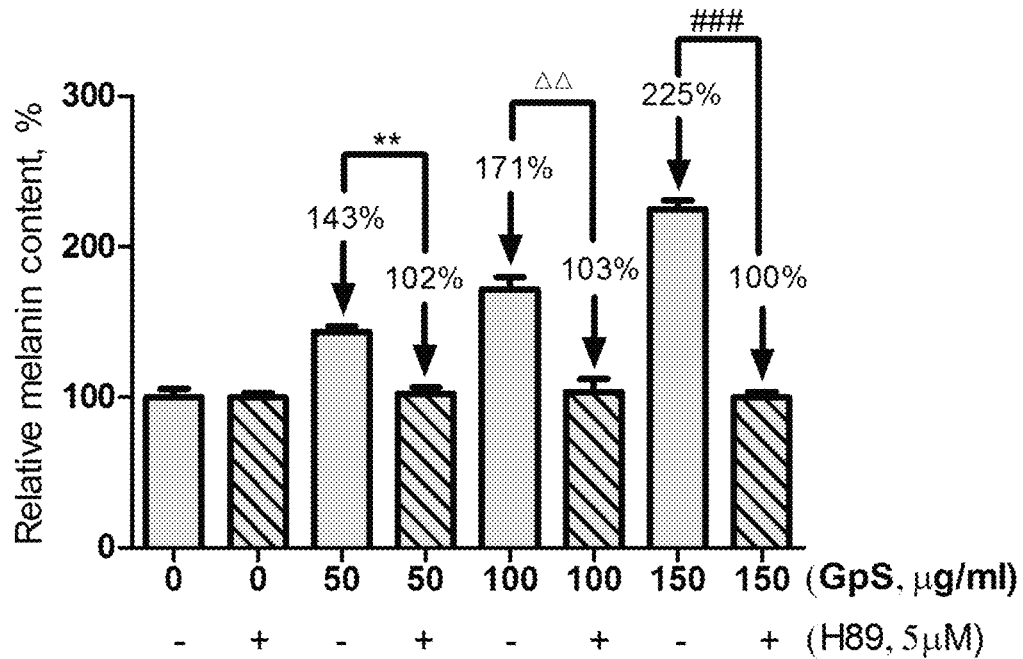
FIG. 7D
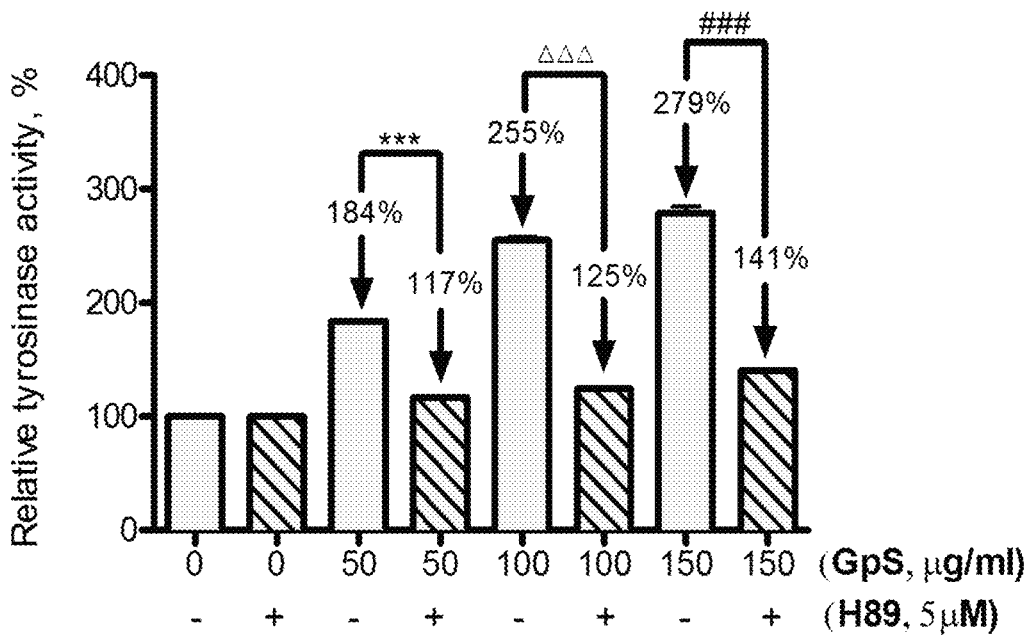
FIG. 7E
FIG. 7

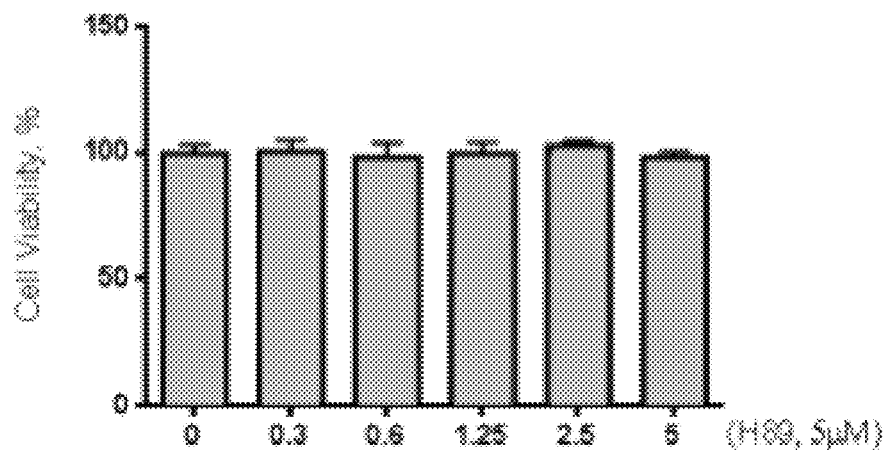
FIG. 8A
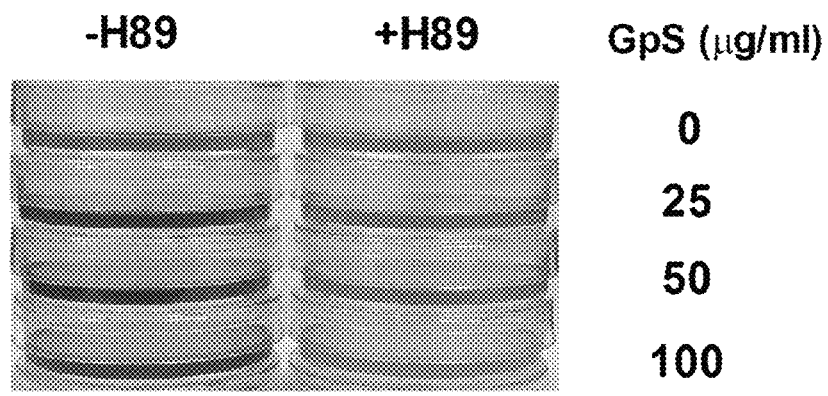
FIG. 8B
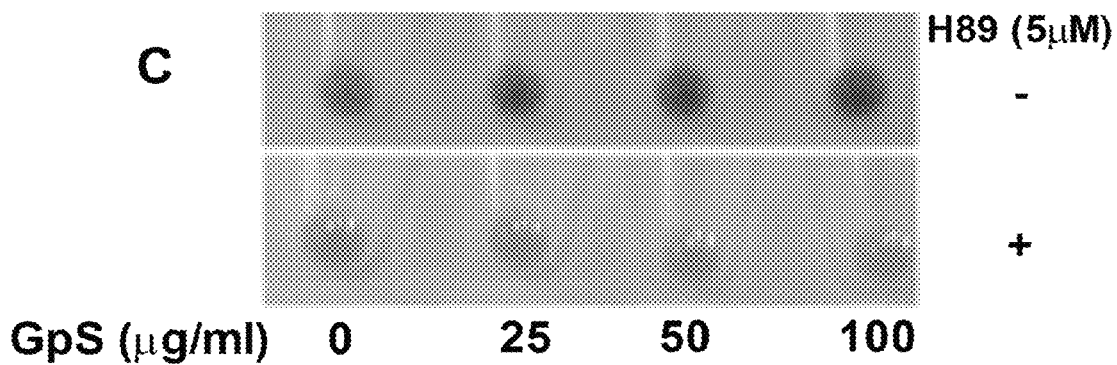
FIG. 8C
FIG. 8

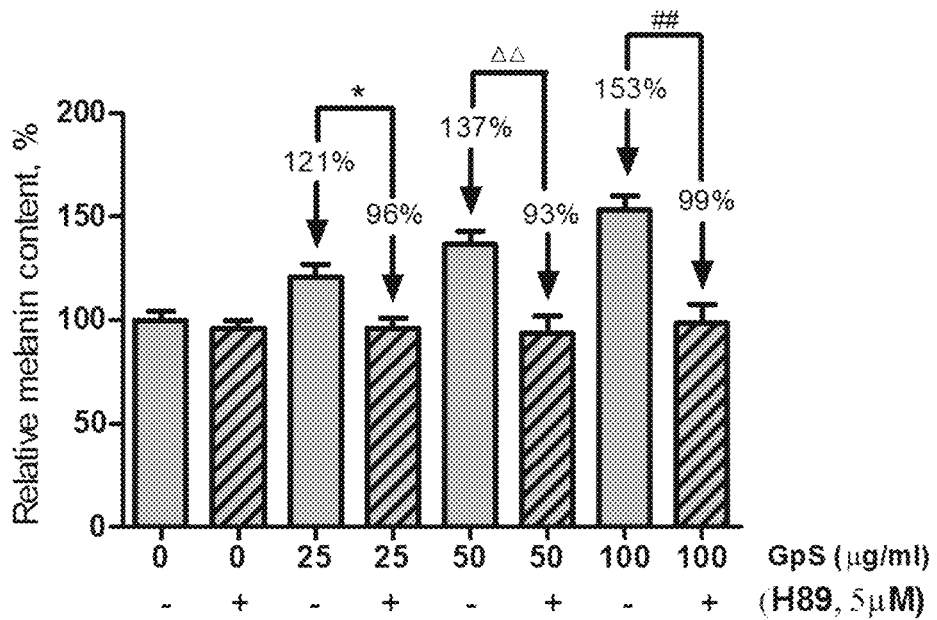
FIG. 8D
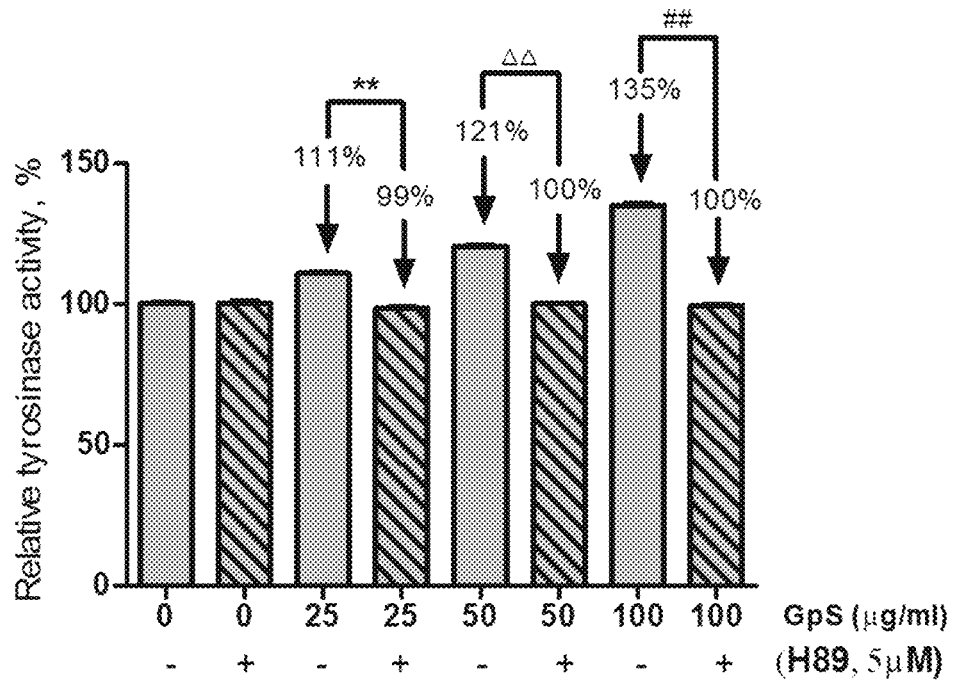
FIG. 8E
FIG. 8

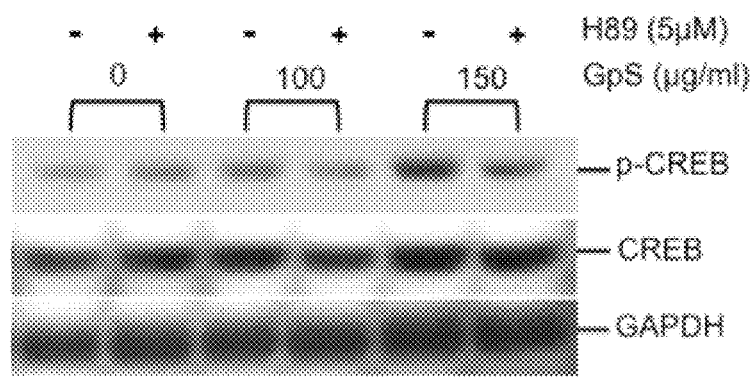
FIG. 9A
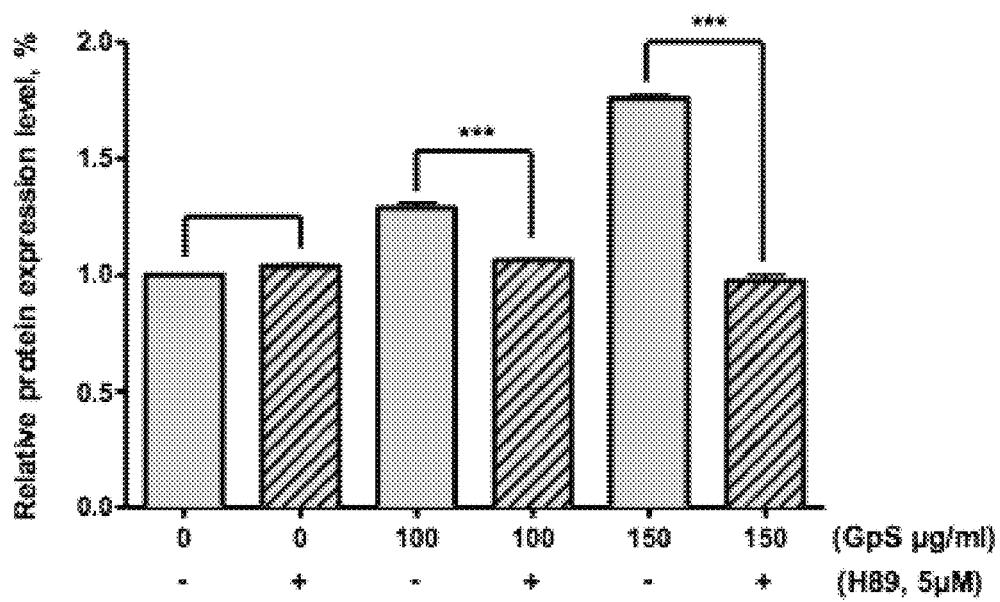
FIG. 9B
FIG. 9

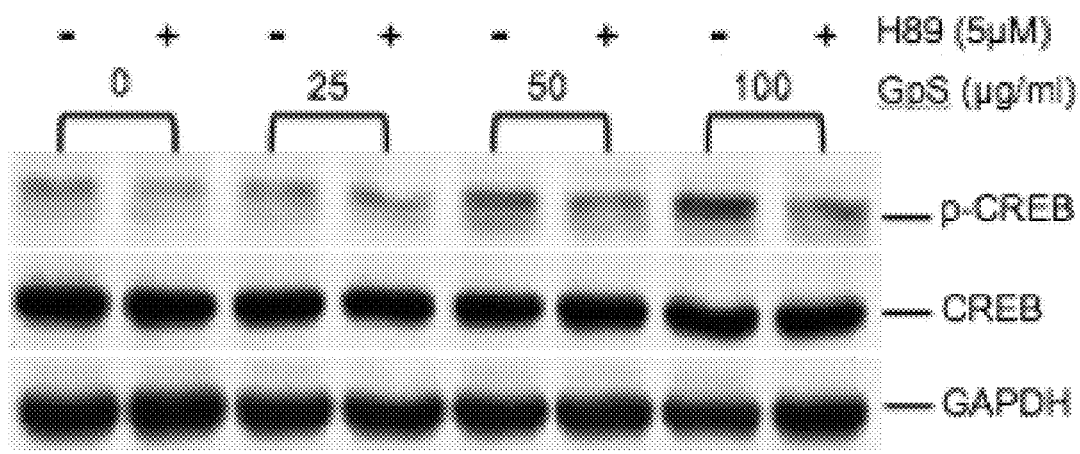
FIG. 10A
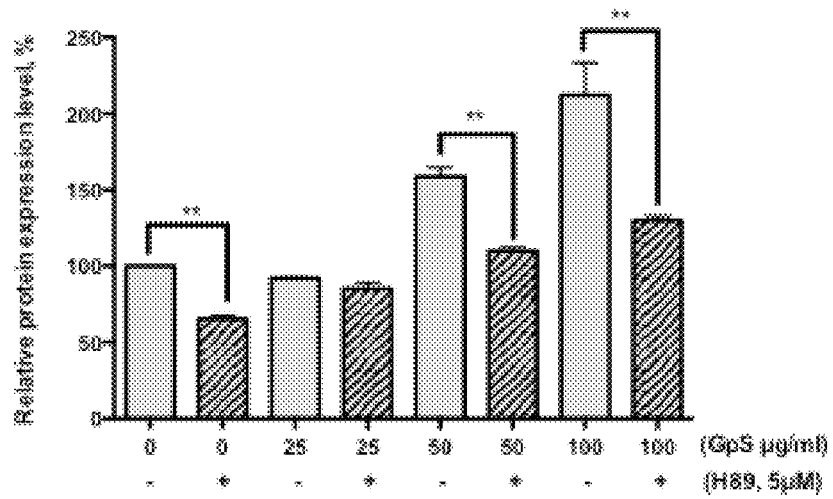
FIG. 10B
FIG. 10

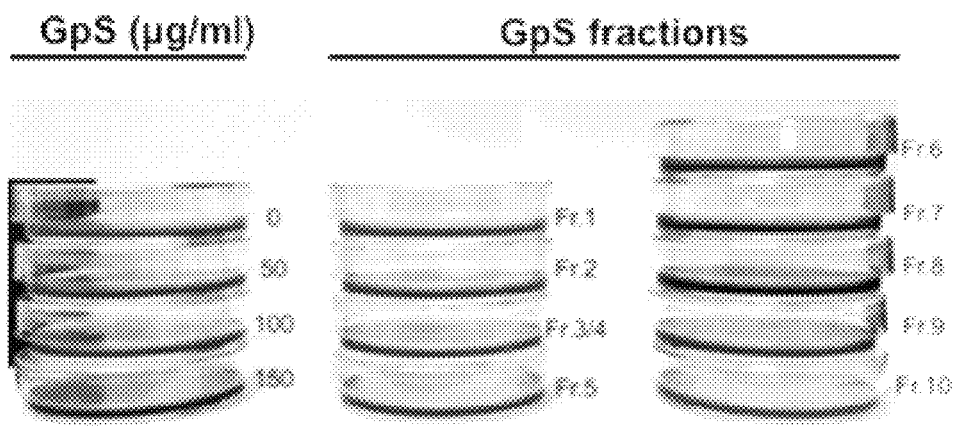
FIG. 12A
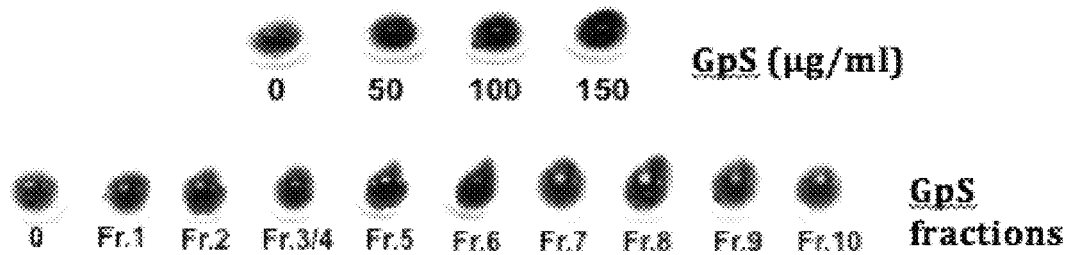
FIG. 12B
FIG. 12

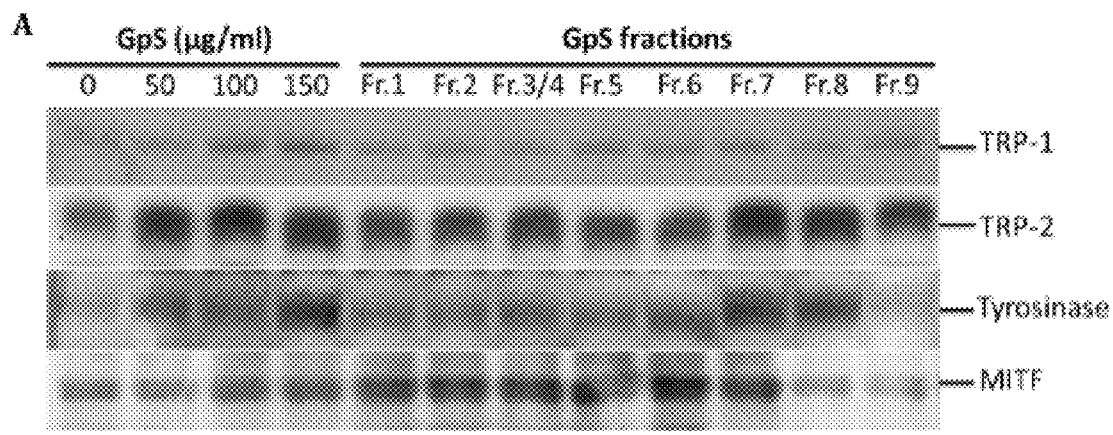
FIG. 13A
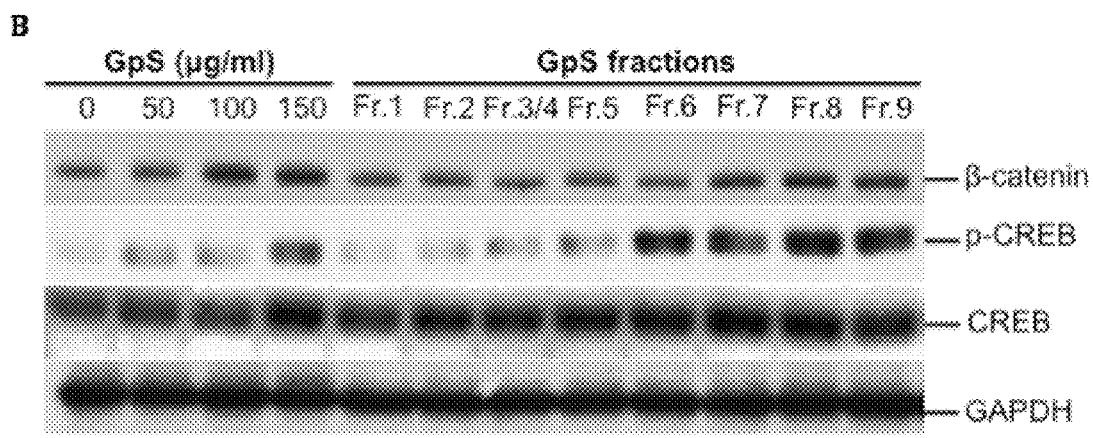
FIG. 13B
FIG. 13

MELANOGENESIS EFFECT OF SAPONINS OF GYNOSTEMMA PENTAPHYLLUM

FIELD OF INVENTION

The present invention relates to saponins fractions isolated from natural sources for its therapeutic uses in melanin production and its melanogenesis effect. More particularly, it relates to saponins fractions extracted from *Gynostemma Pentaphyllum* and their melanogenesis effects.

BACKGROUND OF INVENTION

Nowadays, skin-tanning products are commercially available for cosmetic purposes and also utilized for the clinical treatment of pigmentary disorders such as vitiligo. Vitiligo is acquired pigment disorder that is caused by melanocyte malfunction and depigmentation.

Melanogenesis is a physiological process in response to UV exposure. There are more than 100 distinct genes directly or indirectly involved in the regulation of melanogenesis. In mammals, melanogenesis is directly regulated by three enzymes, tyrosinase (TYR), tyrosinase related protein-1 (TRP-1) and tyrosinase related protein-2 (TRP-2). Tyrosinase is regarded as the rate-limiting enzyme of melanogenesis. It plays a pivotal role in the modulation of melanin production by catalyzing the hydroxylation of tyrosine into dihydroxyphenylalanine (DOPA) and the further oxidation of DOPA into DOPAquinone by tyrosinase. TRP-2, which functions as a DOPAchrome tautomerase, catalyzes the rearrangement of DOPAchrome to 5,6-dihydroxyl indole-2-carboxylic acid (DHICA), whereas TRP-1 oxidizes DHICA to a carboxylated indole-quinone. Microphthalmia-associated transcription factor (MITF) is known to be the master regulator of melanocyte differentiation, pigmentation, proliferation and survival. It is a major transcriptional regulator of the tyrosinase family genes TYR, TRP-1 and TRP-2 responsible for pigmentation.

Protein kinase A (PKA) signaling has been implicated in melanogenesis. PKA can be activated by the elevation of cellular cAMP, and PKA activation can in turn lead to the activation of MITF transcriptional activity through the activation of CREB, resulting in the expression of tyrosinase, TRP-1, and TRP-2 genes. On the other hand, Wnt/β-catenin signaling has also been involved in the melanogenesis based on the finding that β-catenin formed a complex with lymphocyte enhancer factor-1 (LEF-1) to up-regulate expression of the MITF gene. Study also showed that β-catenin directly interacts with the MITF protein itself, then activates MITF-specific target genes.

*Gynostemma pentaphyllum* (Gp) is a perennial creeping herb in the family of Cucurbitaceae. It is widely distributed in China, particularly in the southern region of the Qinling Mountains and the Yangtze River. The earliest documented use of Gp as a vegetable was found in the manuscript titled '*Herbs for Famine*' which was published in the Ming Dynasty (1368-1644 A.D.) The '*Compendium of Materia Medica*', a monumental work in the Chinese medicine field by Li Shi-Zhen, stated that Gp can be used for lowering cholesterol levels, regulating blood pressure, strengthening gastritis, as well as reducing inflammation. Many studies showed that Gp may possess anti-oxidant, anti-apoptotic and anti-carcinogenic properties in vitro and animal studies. Lin C C, Huang P C, Lin J M. Antioxidant and hepatoprotective effects of *Anoectochilus formosanus* and *Gynostemma pentaphyllum*. Am. J. Chinese Med. 2000, 28:87-96 demonstrated that Gp exerts an antioxidant effect and hepatoprotective activity on acetaminophen-induced liver injury in rats; Zhou Z T, Wang Y, Zhou Y M, Zhang S L. Effect of *Gynostemma pentaphyllum* Mak on carcinomatous conversions of golden hamster cheek pouches induced by dimethylbenzanthracene: a histological study. Chinese Med. J. Peking 1998, 111:847-850 demonstrated that Gp could inhibit and reverse the carcinomatous conversions of leukoplasia of golden hamster cheek pouches induced by dimethylbenzanthracene, indicating its positive anti-carcinogenic activities; Chen J C, Chung J G, Chen L D. Gypenoside induces apoptosis in human Hep3B and HA22T tumor cells. Cytobios 1999, 100:37-48 demonstrated that Gp inhibited cell viability through induction of apoptosis in human Hep3B and HA22T tumor cells; Ma Z R and Yang Z B. Scavenging effects of *Astragalus* and *Gynostemma pentaphyllum* with its product on O2 and OH. Zhong Yao Cai 1999, 22:303-6 demonstrated that Gp could scavenge the active oxygen free radicals effectively and Ginsenoside Rb1 extracted from Gp showed a strong effect on scavenging the .OH; and Wang Q F, Chen J C, Hsieh S J, Cheng C C, Hsu S L. Regulation of Bcl-2 family molecules and activation of caspase cascade involved in gypenosides-induced apoptosis in human hepatoma cells. Cancer Lett. 2002, 183:169-78 demonstrated that Gp could induce apoptosis through the up-regulation of Bax and Bak, and down-regulation of Bcl-2, release of mitochondrial cytochrome c and activation of a caspase cascade in human hepatoma Huh-7, Hep3B and HA22T cell lines. Also, it is previously demonstrated in Tai W C S, Zhang S Z H, Jiang Z H, Hsiao W W L. Isolation of Active ingredients with anticancer activity of total triterpenoids saponins of *Gymnostemma Pentaphyllum* by cell-based co-culture activity-guided fractionation assay, 2010, the $9^{th}$ CGCM meeting that GpS can kill GFP/Ras transformed cancer cells in the presence of normal cells in the co-culture assay system, which showed the anti-cancer effect of GpS.

Gp contains over a hundred different triterpenoid saponins that structurally resemble ginseng saponins. Specifically, gypenoside 3 is identical to ginsenoside Rb1, gypenoside 4 is identical to ginsenoside Rb3, gypenoside 8 is identical to ginsenoside Rd, and gypenoside 12 is identical to ginsenoside F2. Many of the other gypenosides are closely related structurally to the ginsenosides and include the 6'-malonyl derivatives characteristic of ginseng. Other constituents reported from Gp include sterols with the ergostane, sholestane, and stigmastane skeletons, and also, the flavonoid glycosides ombuin and ombuoside, rutin, yixingensin, polysaccharides, vitamins, minerals, carotenoids and amino acids.

Citation or identification of any reference in this section or any other section of this application shall not be construed as an admission that such reference is available as prior art for the present application.

SUMMARY OF INVENTION

Accordingly, it is an object of the present invention to provide a composition for inducing melanogenesis effects in an animal comprising an effective amount of saponins extracted from herbal plants and/or an effective mixture thereof.

In a first embodiment of the present invention there are provided herbal plants comprising *Gynostemma pentaphyllum* and its related species.

In a second embodiment of the present invention there are provided saponins comprising effective fraction extracts from said herbal plants and/or effective mixture thereof.

In a third embodiment of the present invention there are provided fraction extracts further comprising derivatives from said fractions and/or effective mixture thereof.

In a fourth embodiment of the present invention there is provided the induction melanogenesis effects in human.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which:

FIG. 3 shows the effects of GpS on melanin production and tyrosinase activity in B16 cells. Cells were treated with indicated concentrations of GpS for 48 hours. FIG. 3A are the cell pellets harvested from the treated culture. FIG. 3B shows effect of GpS on cellular melanin content. FIG. 3C shows effect of GpS on tyrosinase activity. Cell viability, tyrosinase activity and melanin content in control cells were regarded as 100%. Data are expressed as means±SD of three independent experiments. *$p<0.05$, $p<0.01$, *$p<0.001$ vs. controls.

FIG. 4 shows the effects of GpS on melanin production and tyrosinase activity in B16F10 cells. Cells were treated with indicated concentrations of GpS for 48 hours. FIG. 4A are the cell pellets harvested from the treated culture. FIG. 4B shows effect of GpS on cellular melanin content. FIG. 4C shows effect of GpS on tyrosinase activity. Cell viability, tyrosinase activity and melanin content in control cells were regarded as 100%. Data are expressed as means±SD of three independent experiments. *$p<0.05$, $p<0.01$, *$p<0.001$ vs. controls.

FIG. 7 shows the effects of H89 on GpS-induced melanogenesis in B16 cells. B16 cells were treated with designated concentrations of GpS in the presence or absence of 5 µM H89 for 48 hours. Cells treated with DMSO were used as control. FIG. 7A is the MTT assay of cell viability treated with various doses of H89. FIG. 7B is the extracellular melanin contents of treated cultures. FIG. 7C is the cell pellets harvested from the treated cultures. FIG. 7D is the quantitation of melanin content in the treated cultures. FIG. 7E is the tyrosinase activity of the treated cultures. Cell viability and tyrosinase activity in control cells were regarded as 100%. Data are expressed as means±SD of three independent experiments. $p<0.01$, *$p<0.001$ vs. 50 µg/ml GpS-treated group; ΔΔ$p<0.01$, ΔΔΔ$p<0.001$ vs. 100 µg/ml GpS-treated group; ###$p<0.001$ vs. 150 µg/ml GpS-treated group. (E) Tyrosinase activity of the treated cultures. Cell viability and tyrosinase activity in control cells were regarded as 100%.

FIG. 8 shows the effects of H89 on GpS-induced melanogenesis in B16F10 cells. B16F10 cells were treated with designated concentrations of GpS in the presence or absence of 5 µM H89 for 48 hours. Cells treated with DMSO were used as control. FIG. 8A is the MTT assay of cell viability treated with various doses of H89. FIG. 8B is the extracellular melanin contents of treated cultures. FIG. 8C is the cell pellets harvested from the treated cultures. FIG. 8D is the quantitation of melanin content in the treated cultures. FIG. 8E is the tyrosinase activity of the treated cultures. Cell viability and tyrosinase activity in control cells were regarded as 100%. Data are expressed as means±SD of three independent experiments. p<0.01, *p<0.001 vs. 25 μg/ml GpS-treated group; ΔΔp<0.01, ΔΔΔp<0.001 vs. 50 μg/ml GpS-treated group; ###p<0.001 vs. 100 μg/ml GpS-treated group. Tyrosinase activity of the treated cultures. Cell viability and tyrosinase activity in control cells were regarded as 100%.

FIG. 9 shows the effects of H89 on GpS-induced expression levels of p-CREB, CREB in B16 cells. B16 cells were pre-treated with 5 μM H89 for 30 min, and then 0-150 μg/ml GpS with 5 μM H89 or 5 μM H89 were added and incubated for 48 hours. Protein extracts were prepared from each treatment groups. FIG. 9A is western blotting analysis of the protein extract from each treatment groups hybridized with various specific antibodies. GAPDH was used as a protein-loading control. FIG. 9B is densitometric quantitations of the western blots showed in FIG. 9A. Data are expressed as means±SD of three independent experiments. ***p<0.001 vs. controls of GpS without H89.

FIG. 10 shows the effects of H89 on GpS-induced expression levels of p-CREB, CREB in B16F10 cells B16F10 cells were pre-treated with 5 μM H89 for 30 min, and then 0-100 μg/ml GpS with 5 μM H89 or 5 μM H89 were added and incubated for 48 hours. Protein extracts were prepared from each treatment groups. FIG. 10A is western blotting analysis of the protein extract from each treatment groups hybridized with various specific antibodies. GAPDH was used as a protein-loading control. FIG. 10B is densitometric quantitations of the western blots showed in FIG. 10A. Data are expressed as means±SD of three independent experiments **p<0.01 vs. controls of GpS without H89.

FIG. 12A is the extracellular melanin contents of the treated cultures. FIG. 12B is the cell pellets obtained from the treated cultures.

FIG. 13A-B are western blotting analysis of the protein extract from each treatment groups hybridized with various specific antibodies. GAPDH was used as a protein-loading control.

DETAILED DESCRIPTION OF INVENTION

Figure 1:
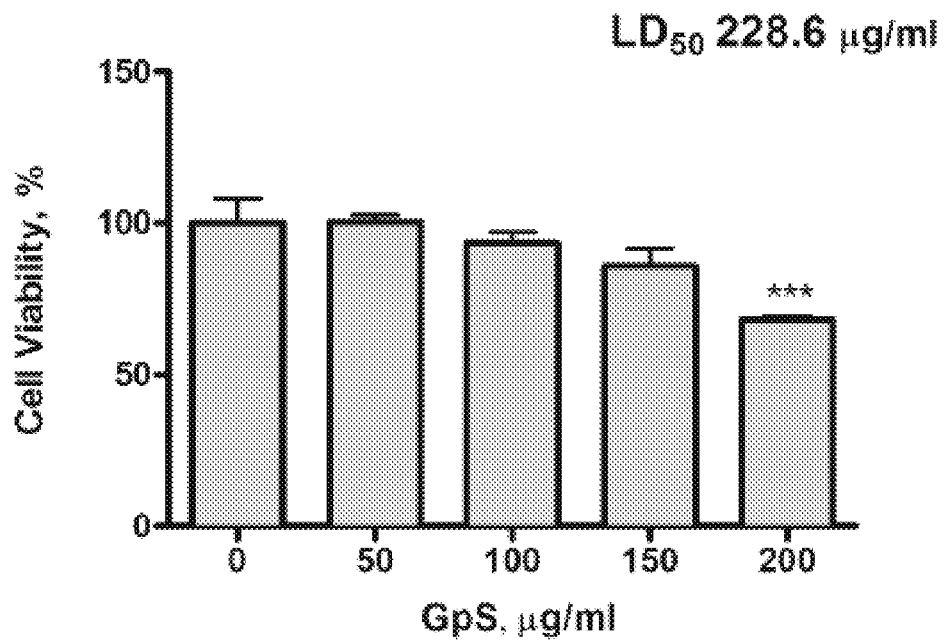
FIG. 1 shows the effects of GpS on cell viability in B16 cells. Cells were treated with indicated concentrations of GpS for 48 hours. Cell viability measured using the MTT assay. Cell viability in control cells were regarded as 100%. Data are expressed as means±SD of three independent experiments. *$p<0.05$ and ***$p<0.001$ vs. controls.

The present invention is not to be limited in scope by any of the specific embodiments described herein. The following embodiments are presented for exemplification only.

Some studies such as Ye Y, Chou G X, Mu D D, Wang H, Chu J H, Leung A K, Fong W F, Yu Z L. Screening of Chinese herbal medicines for antityrosinase activity in a cell free system and B16 cells. *J Ethnopharmacol.* 2010, 129 (3):387-90 previously screened herbal medicines with skin whitening or tanning effects and discovered that herbal medicines, *Ampelopsis japonica, Lindera aggregata*, and *Polygonatum odoratum*, and 3 formulas, Qian-Wang-Hong-Bai-San (QW), Qiong-Yu-Gao, and San-Bai-Tang inhibit the tyrosinase activity, and Gp's ability to stimulate tyrosinase activity has not been reported. The present invention provides Gp and its derived fractions to stimulate tyrosinease and the underlying mechanisms.

Materials & Methods

Reagents

Dimethylsulfoxide (DMSO), 3-(4,5-dimethyl-thiazol-2-yl)-2,5-diphenyl tetrazolium bromide (MTT), Ammonium Persulfate (APS), N,N,N,N'-Tetramethylethylenediamine (TEMED), H89 and L-DOPA were purchased from Sigma (St. Louis, Mo., USA). CREB, p-CREB (Ser 133), GSK3β, p-GSK3β (Ser 9), PKA and p-PKA (Thr 197) antibodies were purchased from Cell Signaling Technology (USA). Antibodies against tyrosinase, MITF, TRP-2, β-catenin and GAPDH antibody were bought from Santa Cruz Biotechnology (USA). TRP-1 antibody was purchased from Abcam Technology (UK). Anti-mouse, anti-goat and anti-rabbit IgG antibodies (horseradish peroxidase conjugated) were purchased from Santa Cruz Biotechnology (USA).

Preparation of GpS

GpS from Fujian Province, sweet taste, 85% purity, was purchased from Hui Zhou Shi Orient Plant Health Care SCL & Tech. CD., Ltd. Dried aerial part of Gp (1 g) was frozen, pulverized and extracted with 15 ml methanol for 30 minutes by sonication at room temperature. The residue was further extracted with 10 ml methanol for 30 minutes sonication at room temperature. The methanol extract were pooled and stored at 4° C. for later usage. Stock solutions of GpS (10 mg/ml) were prepared in milli Q water.

Preparation of GpS Fractions

The GpS were separated by chromatography on a MCI-CHP 20P column (R=2.3 cm, L=30 cm, V=498 ml, gradient elution: 0-100% MeOH, Fr.1: 50%, Fr.2: 60%, Fr.3+Fr.4: 60-70%, Fr.5: 70%, Fr.6: 80%, Fr.7: 80%, Fr.8: 80-90%, Fr.9: 90%, Fr.10: 90-100% MeOH). Each fraction was analyzed by negative-ion UPLC-ESL-MS (ACQUITY UPLC®BEH Shield RP18 1.7 μm 2.1×100 mm Column, Part No. 186002854). The content of saponins in GpS was roughly calculated to be 73.3% based on the isolation yields of the above fractions. Stock solutions of Fr.1, Fr.2, Fr.5, Fr.6 and Fr.7 (40 mg/ml), Fr.3/4 (30 mg/ml) were prepared in milli Q water. Stock solutions of Fr.8, Fr.9 and Fr.10 (40 mg/ml) were prepared in DMSO.

Cell Lines and Culture Medium

Mouse melanoma cell lines B16 and B16F10 purchased from ATCC (USA). All the cells were grown in DMEM medium (Gibco, USA) supplemented with 10% fetal bovine serum (Gibco, USA) and 1% penicillin/streptomycin (Gibco, USA) at 37° C. in a humidified atmosphere of 5% $CO_2$.

Cell Viability Assay

Cell viabilities were determined using the MTT assay. Briefly, cells were seeded in 96-well plates (1×$10^3$ cells/well) and allowed to adhere at 37° C. for 24 hours. Various concentrations of drugs were then added. After 48 hours incubation, 20 μl of MTT solution (2.5 mg/ml in PBS) was added to each well and cells were incubated at 37° C. for 4 hours. Following medium removal, 100 μl of DMSO were added to each well and the plates were gently shaken for 5 minutes. Optical absorbance was determined at 570 nm with a microplate spectrophotometer (BD Bioscience, USA). Absorbance of cells without treatment was regarded as 100% of cell survival. Each treatment was performed in triplicate and each experiment was repeated three times.

Tyrosinase Activity Assay

Cells were seeded in 96-well plates ($3\times10^3$ cells/well) and allowed to adhere at 37° C. for 24 hours. Test samples were then added to individual wells. After 48 hours incubation, cells were washed with ice-cold PBS and 100 μl of 0.1% Triton X-100 lysis buffer were added into each well and lysed at −80° C. for 30 minutes. After freezing and thawing, 100 μl of freshly prepared substrate solution (0.1% L-DOPA) were added into a well on a 96-well plate. Following 2 hours incubation, the absorbance was determined at 475 nm with a microplate spectrophotometer (BD Bioscience, USA). Each percentage value of the drug-treated cells was calculated with respect to that of control cells. Each treatment was repeated three times.

Measurement of Cellular Melanin Contents

Cells were seeded in a 60 mm dish ($2\times10^5$ cells/dish) and allowed to adhere at 37° C. for 24 hours. After adding test samples, cells were incubated for 48 hours and then washed with PBS and lysed in 120 μl of 1 M NaOH followed by 10 minutes of heating at 100° C. to solubilize the melanin. Each lysate (100 μl) was added into a well of a 96-well microplate, and the absorbance was determined at 475 nm with a microplate spectrophotometer (BD Bioscience, USA). The protein concentration of each sample was determined by DC Protein Assay (BIO-RAD, USA). Each experiment was repeated three times. The intracellular melanin amount/protein amount was shown as percentage values. Each percentage value of the drug-treated cells was calculated with respect to that of control cells.

Preparation of Total Protein Lysates

Cells were collected and total protein lysates were extracted with RIPA lysis buffer [50 mM Tris-Cl, 1% v/v NP-40, 0.35% w/v sodium-deoxycholate, 150 mM NaCl, 1 mM EDTA, 1 mM EGTA, 1 mM phenylmethylsulfonyl fluoride (PMSF), 1 mM NaF, 1 mM $Na_3VO_4$, pH adjusted to 7.4] containing a protease inhibitor cocktail (Roche, Germany) for 30 minutes on ice. After centrifugation at 20,800×g for 15 minutes at 4° C., the supernatant was collected and regarded as total cell lysates.

Determination of Protein Concentration

Protein concentration was determined by DC Protein Assay (Bio Rad, USA). A standard curve was created by bovine serum albumin (BSA) concentration 0, 0.375, 0.75 and 1.5 μg/μl for the determination of the absolute protein concentration. Then, the mixture of reagent A and reagent S (50:1) was mixed with 5 μl of protein lysate. Then 200 μl of reagent B were added and mixed with 10 minutes incubation at room temperature. Finally, the absorbance was determined at 700 nm with a microplate spectrophotometer (BD Bioscience, USA).

Western Blotting

After the determination of the protein concentration, equal amounts of protein lysate and 5×SDS loading buffer (50 mM Tris-HCl pH7.5, 200 mM NaCl, 2 mM EDTA, 10% (v/v) glycerol, 1% Triton X-100, 0.01% (w/v) bromophenol blue) were mixed together and boiled for 5 minutes at 100° C. Equal amount of individual protein samples were separated within the running buffer (25 mM Tris-base, 250 mM glycine, 0.1% (w/v) SDS) at 150 V for 100 minutes by 10% SDS-PAGE gel and then electro-transferred onto 0.45 μM Biotrace hydrophobic polyvinylidene fluoride membrane (PVDF) (Pall, USA) using the wet-transfer system (Bio-Rad, USA) in the ice-cold transfer buffer (25 mM Tris, 190 mM glycine and 10% (v/v) MeOH) for 120 minutes at 200 mA.

Immunoblotting

Membranes were blocked for 30 minutes with 3% Bovine Serum Albumin in TBST buffer composed of 50 mM Tris (pH 7.6), 150 mM NaCl and 0.1% Tween-20 and incubated with the primary antibody overnight at 4° C. GADPH was used as loading control and was detected using an anti-GADPH polyclonal antibody (Santa cruz Biotechnology). Then, membranes were washed with TBST for 10 minutes three times and then probed with their respective horseradish peroxide conjugated secondary antibody (1:5000) for 1 hour at room temperature. Similarly, membranes were washed with TBST for 10 minutes three times and finally Enhanced Chemiluminescence detection reagents (GE Healthcare, UK) were used to detect signals.

Statistical Analysis

Results were expressed as the mean±S.D. Differences between the two groups were analyzed using the Student's t test. Densitometric analysis of Western blotting was processed by Quantity one (Bio Rad, USA).

Results

Figure 2:
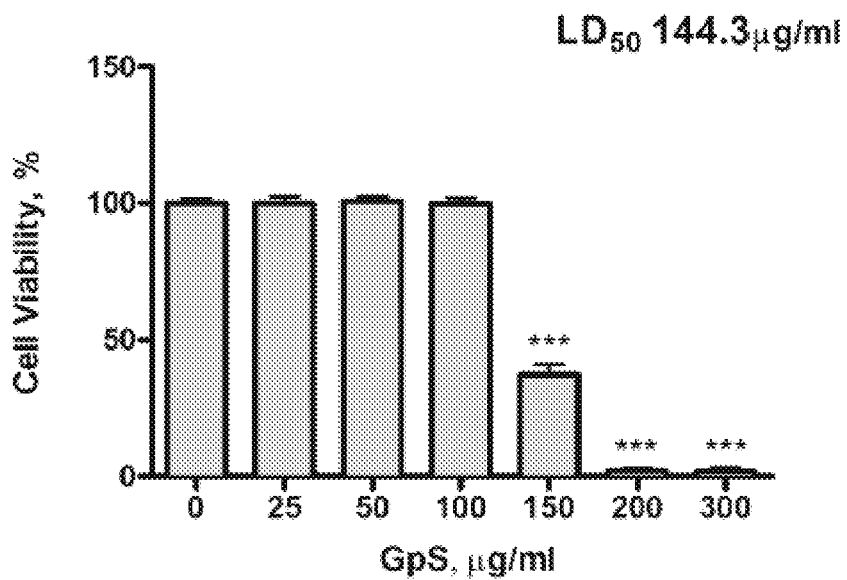
FIG. 2 shows the effects of GpS on cell viability in B16F10 cells. Cells were treated with indicated concentrations of GpS for 48 hours. Cell viability measured using the MTT assay. Cell viability in control cells were regarded as 100%. Data are expressed as means±SD of three independent experiments. ***$p<0.001$ vs. controls.

GpS Stimulates Tyrosinase Activity and Melanin Synthesis in B16 and B16F10 Cells at Non-Cytotoxtic Dosages Cytotoxicity of GpS to B16 and B16F10 cells are tested by MTT cell proliferation assay. The results show that 48 hours treatment of GpS dosages at 50 and 100 μg/ml show no cytotoxicity and mild cytotoxicity at the dosage of 150 μg/ml in B16 cells (FIG. 1), but show high cytotoxicity to B16F10 cells (FIG. 2). Thus, dosages from 50 to 150 μg/ml and 25 to 100 μg/ml are chosen to determine the effects of GpS on tyrosinase activity and melanin synthesis in B16 and B16F10 cells respectively. Treatment with GpS demonstrates a dose-dependent induction of melanin formation and tyrosinase activity in B16 cells. From 50 to 150 μg/ml of GpS, the melanin content increases by 43%, 79% and 113%, respectively (FIG. 3B), and the tyrosinase activity increases by 84%, 155% and 179%, respectively (FIG. 3C). Although treatment of 150 μg/ml GpS caused mild cytotoxicity to B16 cells, it contributes the strongest effect on induction of melanogenesis. These results demonstrate that GpS can effectively induce pigmentation in B16 cells. On the other hand, treatment with GpS in B16F10 cells show milder induction of melanin formation and tyrosinase activity compared with B16 cells (FIG. 4).

Figures 5, 5A:
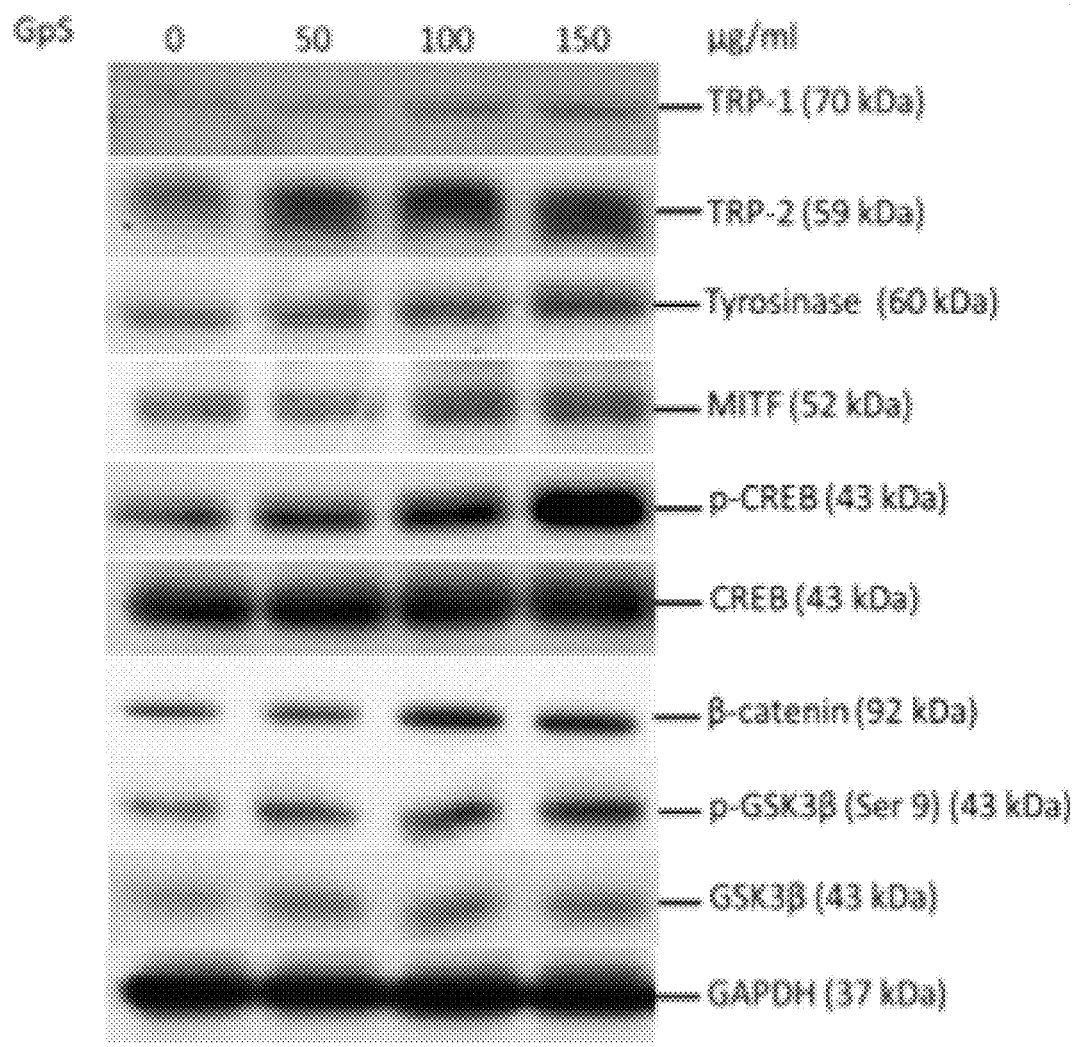
FIG. 5 shows the effects of GpS on the expression levels of melanogenic proteins in B16 cells. B16 cells were treated with GpS from 50 to 150 µg/ml for 48 hours. Protein extracts were prepared from each treatment groups.
FIG. 5A is western blotting analysis of the protein extract from each treatment groups hybridized with various specific antibodies. GAPDH was used as a protein-loading control.
Figures 5, 5B:
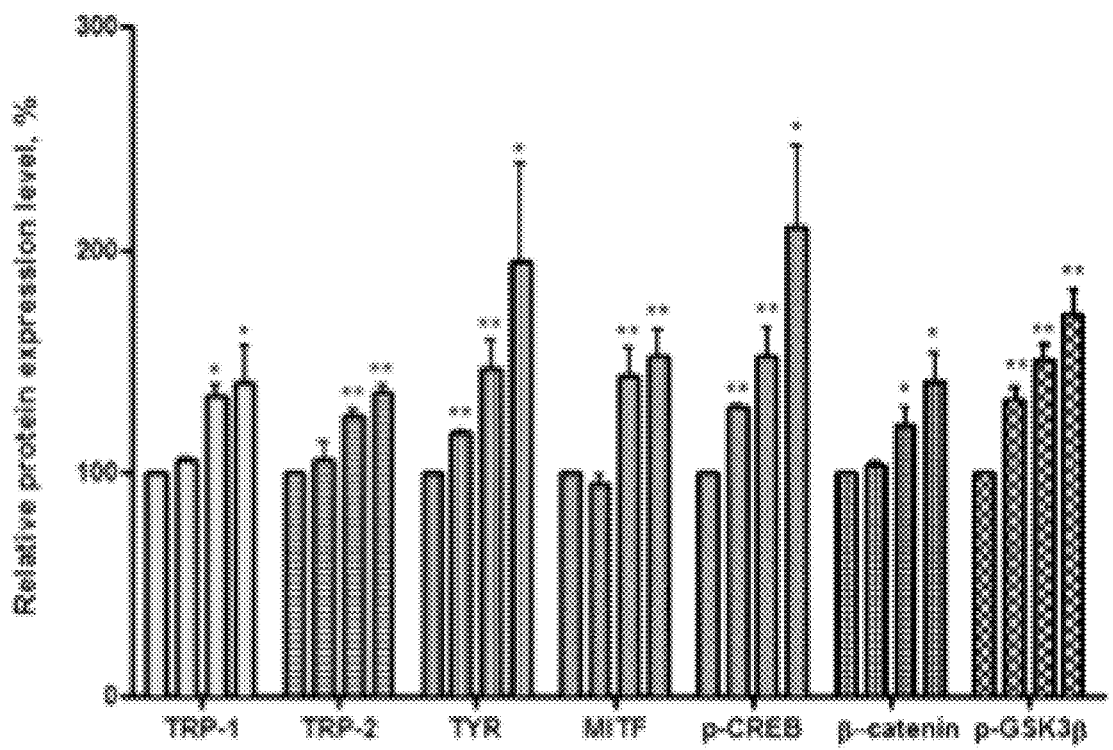
FIG. 5B is the densitometric quantitations of the western blots showed in FIG. 5A. Data are expressed as means±SD of three independent experiments. *$p<0.05$, $p<0.01$, *$p<0.001$ vs. controls.
Figures 6, 6A:
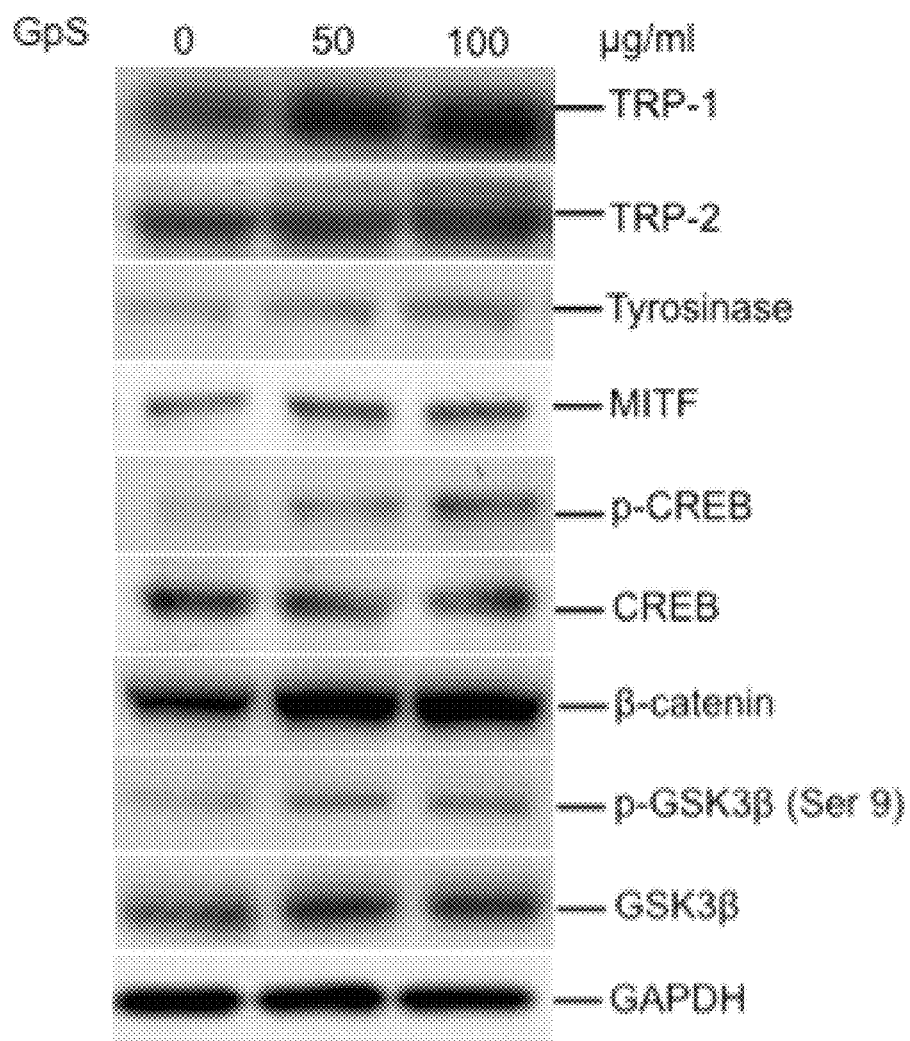
FIG. 6 shows the effects of GpS on the expression levels of melanogenic proteins in B16F10 cells. B16F10 cells were treated with GpS from 50 to 100 µg/ml for 48 hours. Protein extracts were prepared from each treatment groups.
FIG. 6A is the western blotting analysis of the protein extract from each treatment groups hybridized with various specific antibodies. GAPDH was used as a protein-loading control.
Figures 6, 6B:
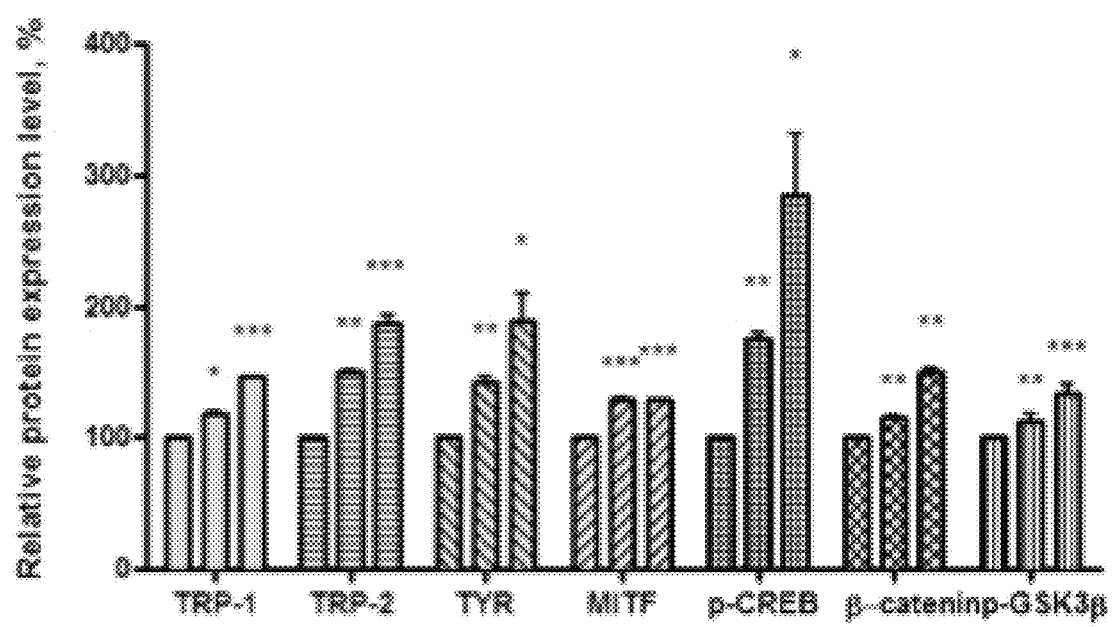
FIG. 6B is the densitometric quantitations of the western blots showed in FIG. 6A. Data are expressed as means±SD of three independent experiments. *$p<0.05$, $p<0.01$, *$p<0.001$ vs. controls.

GpS Up-Regulates the Levels of Protein Expression of the Melanogenic Molecules in B16 and B16F10 Cells The melanin synthesis requires three main enzymes for proper production. They are tyrosinase, TRP-1 and TRP-2, and convert the tyrosine into melanin finally, but more importantly, MITF is the master regulator in controlling the expression of these three enzymes. To explore the mechanisms underlying the induction of the melanogenic activity of GpS, the effects of GpS on MITF, tyrosinase, TRP-1 and TRP-2 protein expression by Western blotting in B16 and B16F10 cells are shown in FIG. 5. The results show that GpS treatment in the dosage of 50 to 150 μg/ml for 48 hours significantly induces MITF, tyrosinase, TRP-1 and TRP-2 expression levels in B16 cells. Treatment with GpS at 150 μg/ml shows the strongest induction effect despite it having mild cytotoxicity to B16 cells. On the other hand, GpS treatment in the dosage of 50 to 100 μg/ml for 48 hours significantly up-regulates MITF, tyrosinase, TRP-1 and TRP-2 expression level in B16F10 cells (FIG. 6).

GpS Induces the β-Catenin and Phosphorylation of CREB in B16 and B16F10 Cells

GpS can induce the expression of MITF, tyrosinase, TRP-1 and TRP-2. The Wnt/β-catenin and PKA involvement in the induction of melanogenic activity of GpS, and the impact of GpS on β-catenin and phosphor-CREB (p-CREB) are shown in Western blotting (FIG. 5, FIG. 6). At the concentrations of 50 to 150 μg/ml and 50 to 100 μg/ml, GpS induce β-catenin and p-CREB expressions without significant influence on total CREB expression in B16 and B16F10 cells respectively. It is known that cAMP/PKA can modulate GSK3β activity through the phosphorylation of GSK3β at the Ser9 site. The expression of phosphorylation of GSK3β at Ser9 is investigated to confirm GSK3β's involvement, through the cAMP/PKA pathway, in up-regulating β-catenin. It is shown that GpS induces the p-GSK3β at Ser9 expressions without any significant influence on total GSK3β expression in B16 and B16F10 cells. It is evident that GpS mediates hyper-pigmentation in B16 and B16F10 cells through the activation of the cAMP/PKA pathway which activates the Wnt/β-catenin pathway.

H89 Attenuates GpS-Induced Elevation of Tyrosinase Activity and Melanin Content in B16 and B16F10 Cells The PKA signaling pathway is known to take part in regulating melanogenic events. Results show that the melanogenic activity of GpS functions through the PKA signaling pathway. To further investigate the involvement of the PKA pathway in the induction of the melanogenic effect of GpS in B16 and B6F10 cells, a PKA inhibitor, H89, is employed. It is demonstrated that H89 imposes no cytotoxicity to B16 and B16F10 cells up to 5 μM for a duration of 48 hours (FIG. 7A, FIG. 8A). Cells are treated with GpS in the presence or absence of H89 inhibitor. The results show that GpS stimulates pigment formation in a dosage dependent manner by examining the colour of the culture medium as well as the cell pellets from the GpS-treated cell cultures. H89 treatment effectively lightens the color of the culture medium as well as the cell pellets. Melanin content and the cellular tyrosinase activity are significantly increased in cells treated with GpS at 50-150 μg/ml and 50-100 μg/ml in B16 and B16F10 cells respectively, and the increments are significantly attenuated by 5 μM H89 (FIGS. 7B &C, FIGS. 8B&C). The cell pellets are significantly darkened after treatment of GpS compared with non-treated control cells, and the cells co-treated with 5 μM H89 and GpS are lighter in color compared with GpS-treated cells (FIG. 7D, FIG. 8D). Also, GpS dose-dependently induces the melanin secretion; however, the secretion of melanin induced by GpS are attenuated after co-treatment with H89 (FIG. 7E, FIG. 8E).

H89 Attenuates GpS-Induced Up-Regulation of p-CREB Expression in B16 and B16F10 Cells To further determine whether the PKA pathway is involved in the induction of melanogenic activity of GpS, the impact of GpS on CREB phosphorylation is examined by Western blotting. The GpS significantly up-regulates p-CREB expression at the dosages from 10 to 150 μg/ml. Application of 5 μM H89 in GpS-treated cells significantly attenuates the GpS-induced p-CREB expression without significant influence on total CREB expression in B16 cells. (FIG. 9). On the other hand, GpS significantly up-regulates p-CREB expression at the dosages from 50 to 100 μg/ml. Application of 5 μM H89 in GpS-treated cells significantly attenuates the GpS-induced p-CREB expression without significant influence on total CREB expression in B16F10 cells (FIG. 10).

Identification of the Active Fractions of GpS in Melanin Production

Figures 11, 11A:
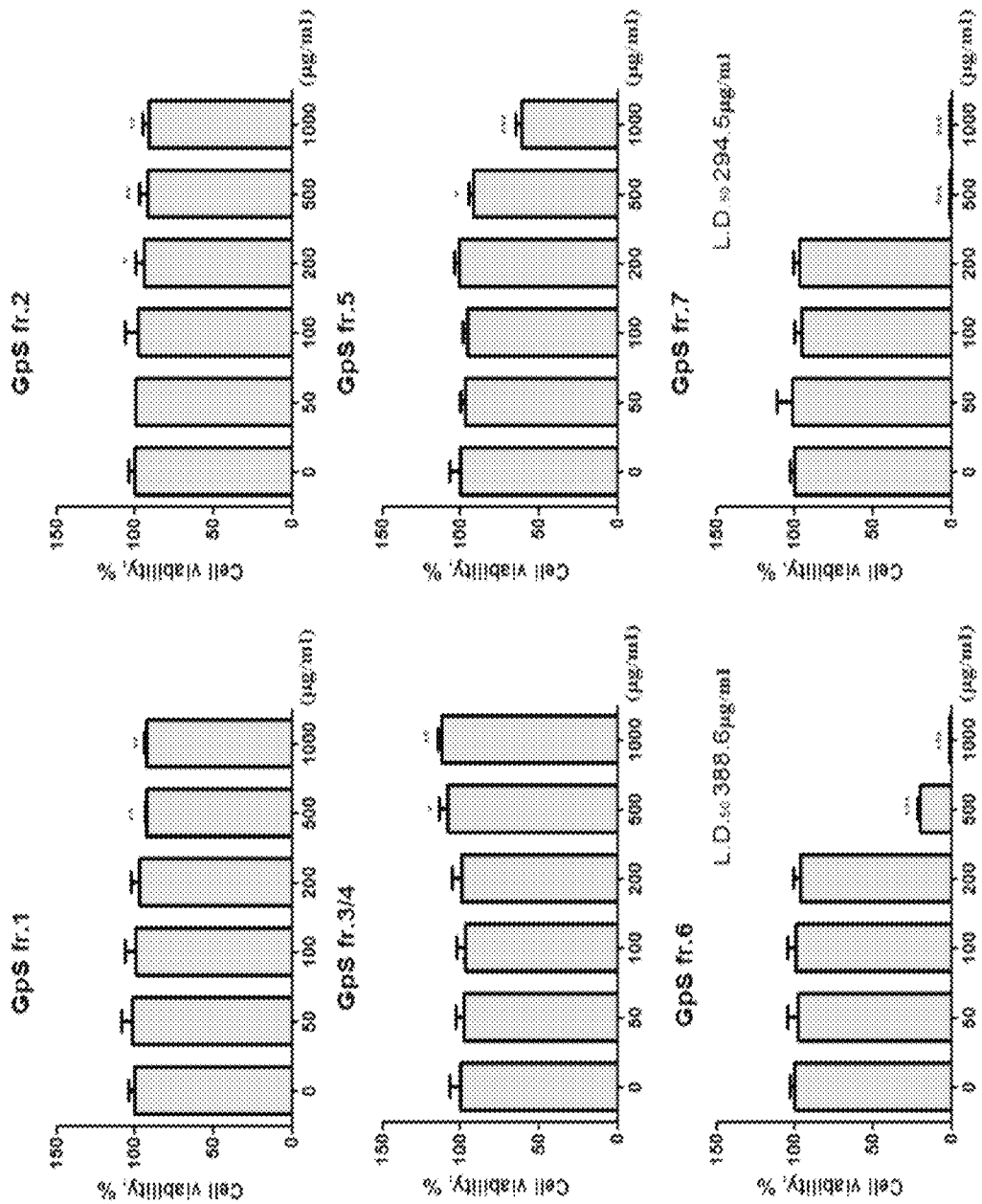
FIG. 11A and FIG. 11B shows the MTT assays of fractions of GpS in B16 cells. Fractions 1-10. B16 cells were treated with designated concentrations of GpS fractions for 48 hours. Cell viability was measured by the MTT assay.
Figures 11, 11B:
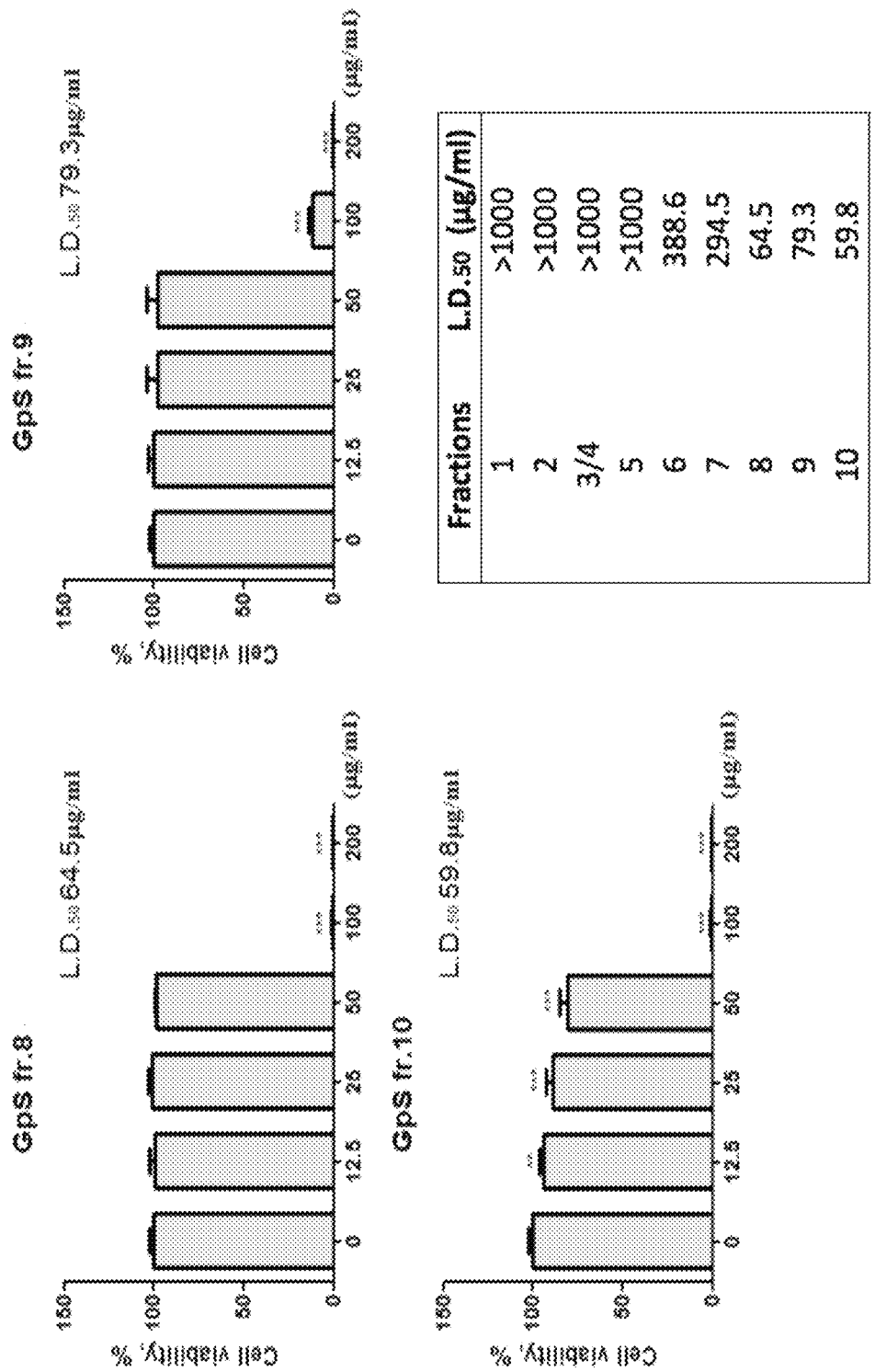
Figures 12, 12C:
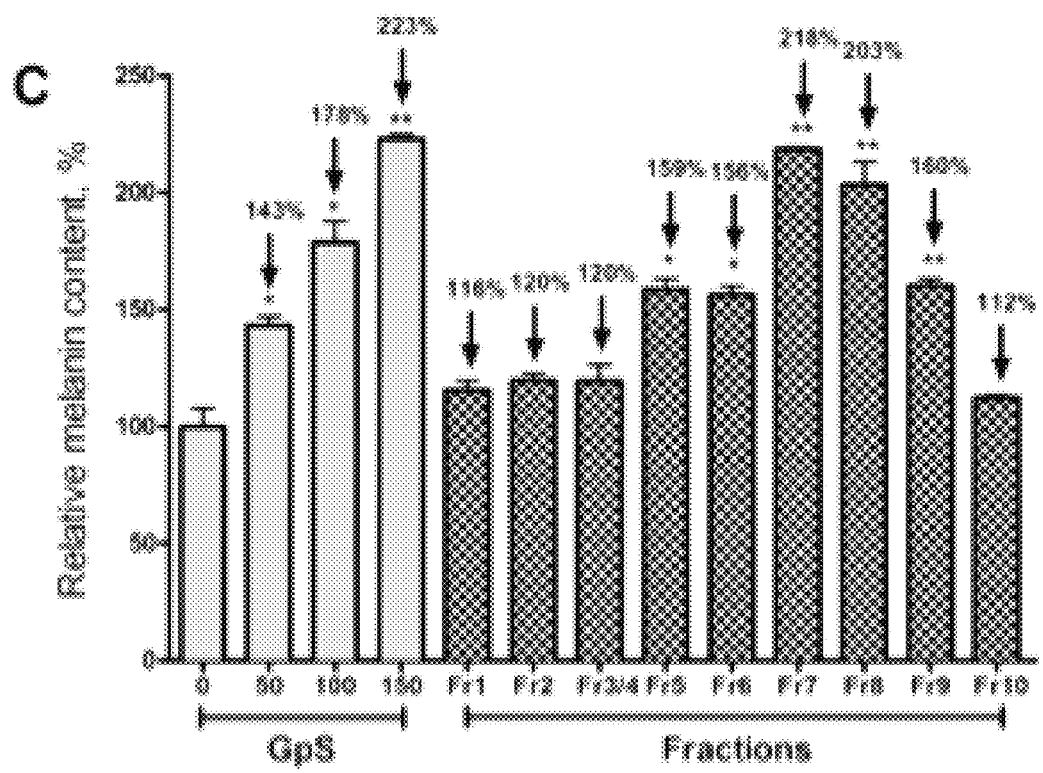
FIG. 12 shows the effects of GpS fractions on melanogenesis in B16 cells. B16 cells were treated with designated concentrations of GpS fractions for 48 hours. Non-toxic dosage of each fraction was used to treat B16 cells (Fr1-Fr7: 200 μg/ml, Fr8 and Fr9: 60 μg/ml, Fr10: 50 μg/ml).
FIG. 12C is the quantification of melanin content in the tested cultures.
Figures 12, 12D:
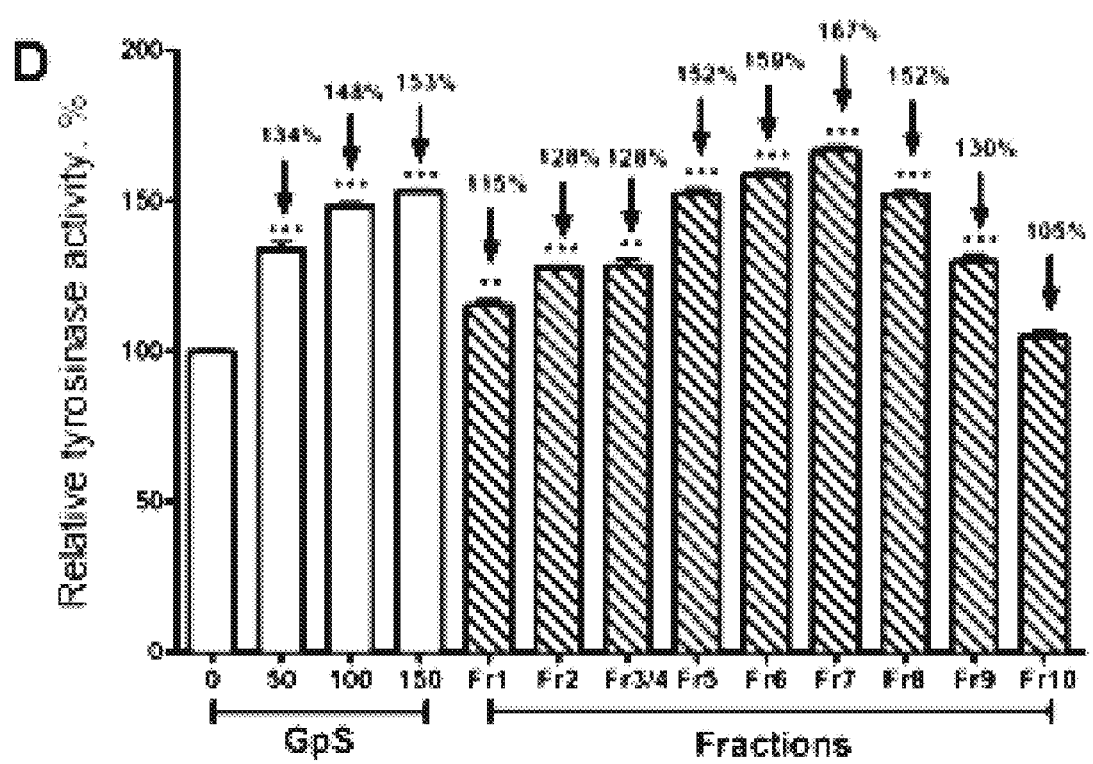
FIG. 12D is the tyrosinase activity of the treated cultures. Cell viability, melanin contents and tyrosinase activity in the no treatment control were regarded as 100%. Data are expressed as means±SD of three independent experiments. *p<0.05, p<0.01, *p<0.001 vs. control group.

GpS Fractions Stimulate Melanin Synthesis and Tyrosinase Activity in B16 Cells at Non-Cytotoxic Dosages GpS is the major constituents of Gp, which is the total saponins of Gp. These major constituents are extracted from the aerial part of Gp. In order to investigate which components of GpS contribute to the induction of the melanogenic effect, the GpS is separated by chromatography to obtain the fractions of GpS, Fr.1 to Fr.10 (Table 1). MTT assay determines whether the fractions of GpS are cytotoxic to B16 cells. The results show that 48 hours treatment of GpS Fr. 1-7 cause no cytotoxicity at the dosage of 200 μg/ml, but GpS Fr.8 and 9 cause no cytotoxicity at the dosage of 50 μg/ml (FIG. 11). Thus, 200 μg/ml and 60 μg/ml are chosen to determine the effects of GpS Fr.1-7 and Fr.8-9 on melanin synthesis and tyrosinase activity, respectively. For the GpS Fr.10, 50 μg/ml is selected as the treatment dosage. The results clearly show that Fr.6-8 induce the secretion of melanin to the medium and Fr. 1-9 induce darker cell pellets (FIGS. 12A & B). Treatment with GpS Fr.7 & 8 show the strongest effect on melanogenic induction upon the isolation yields of the fractions from the total GpS (FIG. 12C). Also, Fr.5-9 show the induction of tyrosinase activity in B16 cells upon the isolation yields of the fractions from the total GpS (FIG. 12D).

TABLE 1

Fractionation of total GpS.

| Fraction No. | Yield of the fraction (%) | % of MeOH |
| --- | --- | --- |
| 1 | 3.2 | 50 |
| 2 | 2.8 | 60 |
| 3 and 4 | 24.4 | 60-70 |
| 5 | 23 | 70 |
| 6 | 4.3 | 80 |
| 7 | 3.5 | 80 |
| 8 | 10.6 | 80-90 |
| 9 | 0.3 | 90 |
| 10 | 1.2 | 90-100 |

The total GpS are separated by chromatography on a MCI-CHP 20P column (R=2.3 cm, L=30 cm, V=498 ml, gradient elution: 0%-100% MeOH). Each fraction is analyzed by a negative-ion UPLC-ESI-MS (ACQUITY UPLC®BEH Shield RP18 1.7 μm 2.1×100 mm Column, Part No. 186002854).

Figures 13, 13C:
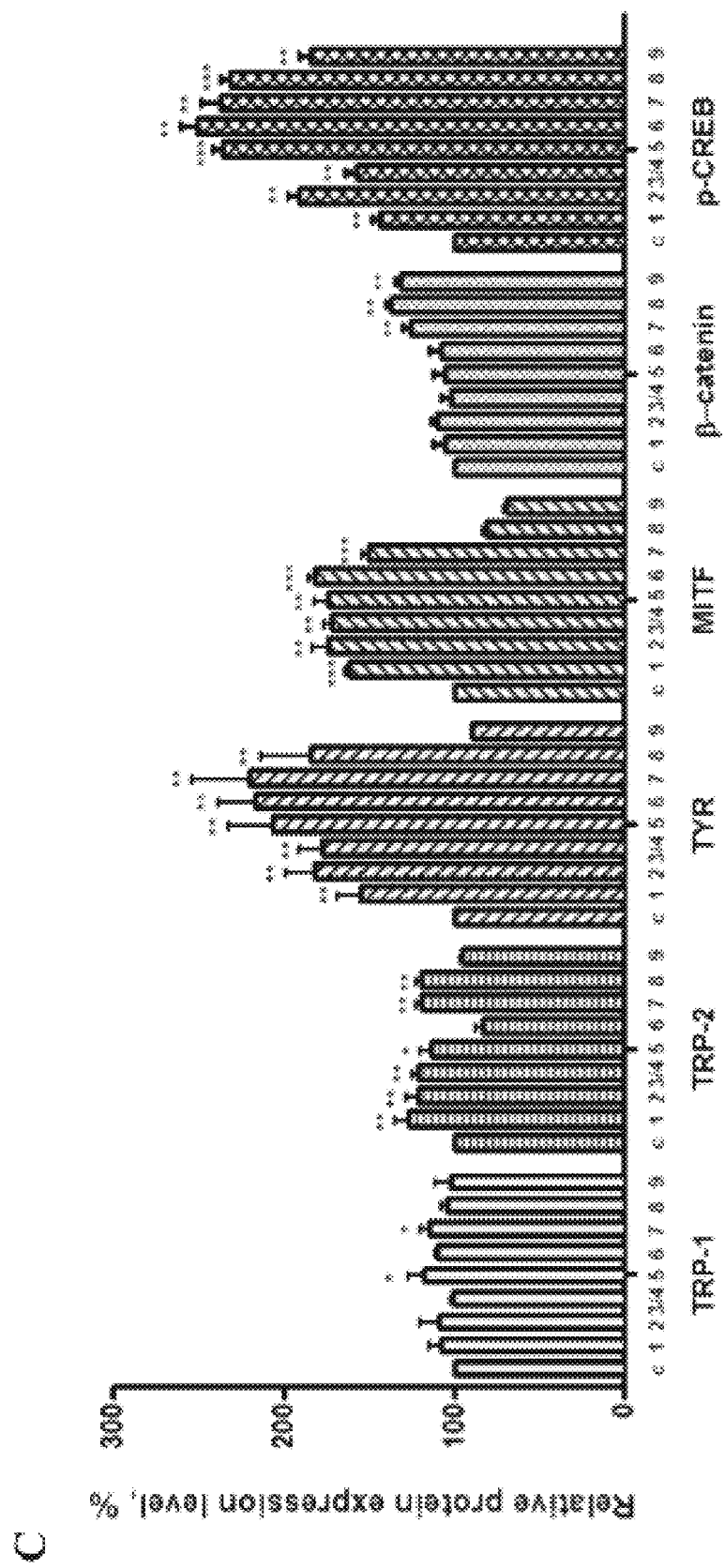
FIG. 13 shows the effects of GpS fractions on the expression levels of melanogenic proteins in B16 cells. B16 cells were treated with non-toxic dosages of GpS fractions for 48 hours. The dosages of fractions treated on B16 cells are as follows, Fr1-Fr7: 200 μg/ml, Fr8 and Fr9: 60 μg/ml. Protein extracts were prepared from each treatment groups.
FIG. 13C is densitometric quantitations of western blots showed in FIGS. 13A & 13B. Data are expressed as means±SD of three independent experiments. *p<0.05, p<0.01, *p<0.001 vs. controls.

GpS Fractions Up-Regulates the Levels of Protein Expression of MITF, Tyrosinase, TRP-1 and TRP-2 in B16 Cells To explore which fractions contribute to the induction of the melanogenic activity of GpS fractions, GpS fractions' ability to up-regulate the melanogenic molecules are investigated by Western Blotting. As Fr.10 does not appear to have any effect on tyrosinase activity and melanin content, only Fr.1-9 are tested. The results show that treatment of GpS Fr.7 for 48 hours significantly induce MITF, tyrosinase, TRP-1 and TRP-2 expression levels (FIG. 13A).

GpS Fractions Induce β-Catenin and Phosphorylation of CREB in B16 Cells

Effects of GpS fractions to up-regulate the expression of β-catenin and p-CREB are investigated, as total GpS does. Results show that GpS Fr.7-9 significantly up-regulate the expression of β-catenin and Fr. 5-9 significantly up-regulate the expression of p-CREB. GpS Fr.7-9 induce both the expression of β-catenin and p-CREB (FIG. 13B).

Discussion

Figure 14:
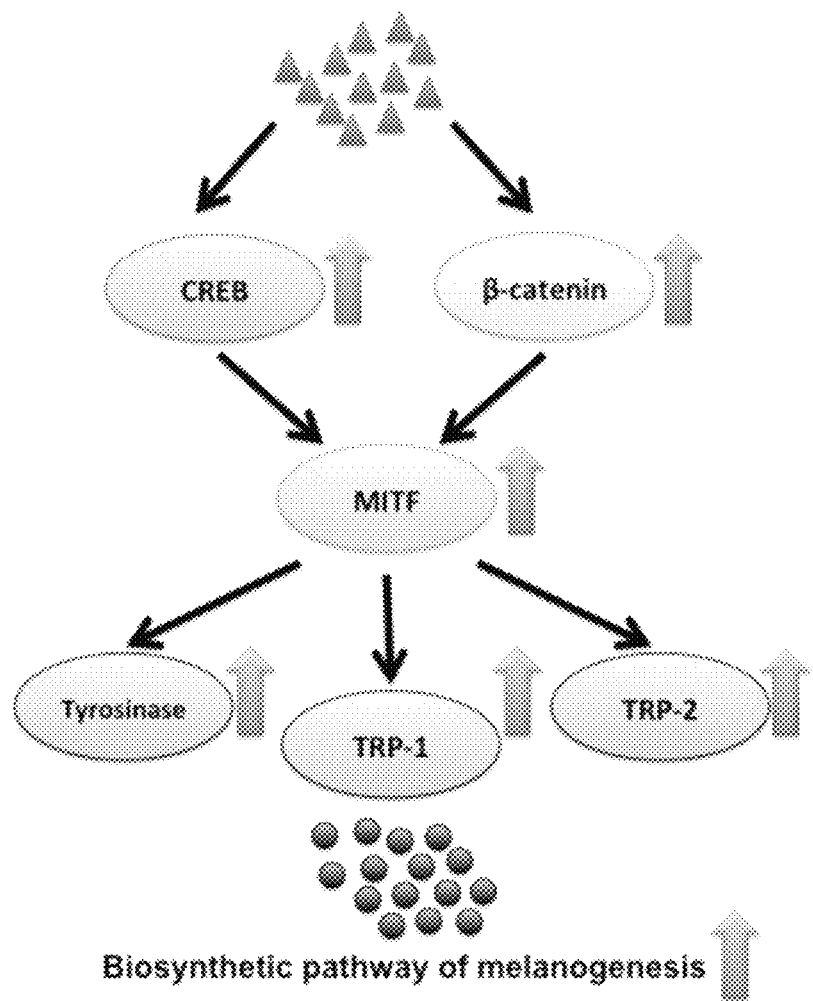
FIG. 14 shows the proposed mechanism involved in GpS mediated melanogenesis

It is demonstrated that GpS induces melanogenesis and tyrosinase activity and up-regulates the expression of TRP- 1, TRP-2, tyrosinase and MITF, and also p-CREB, β-catenin and p-GSK3β (Ser9). PKA signaling is an important pathway modulating melanogenesis. There is evidence that cellular cAMP is a major intracellular signaling cascade critical to pigmentation. H89, the PKA inhibitor, can decrease intracellular cAMP content by activating cAMP phosphodiesterase. cAMP-induce elevation of melanogenesis is mediated by PKA, which phosphorylates the CREB family transcription factors. Once phosphorylated, CREB can upregulate MITF which binds to M-box and E-box motifs in the promoter of target genes including melanogenesis for transcriptional up-regulation of the key enzyme in melanin production. The results show that H89 significantly blocks GpS-induced p-CREB up-regulations and inhibit GpS-stimulated increases of cellular melanin content and tyrosinase activity, proving that the PKA signaling pathway also plays a role in the induction of the melanogenic effect of GpS. On the other hand, Wnt/β-catenin signaling and melanocyte differentiation has been revealed by the finding that β-catenin, which accumulates with activation of Wnt/β-catenin signaling, forms a complex with lymphocyte enhancer factor-1 to up-regulate expression of the MITF gene. Also, β-catenin directly interacts with the MITF protein itself and then activates MITF-specific target genes. It is known that activation of the cAMP/PKA pathway stimulates the phosphorylation of β-catenin at the Ser675 site and phosphorylation of GSK3β at the Ser9 site which inhibit the activity of GSK3β and inhibit the degradation of β-catenin and facilitate the translocation into nuclear to initiate the transcription of the Wnt/β-catenin target genes. GpS can activate the expression of β-catenin and MITF, which in turn up-regulates the expression of tyrosinase, TRP-1 and TRP-2 inducing melanin production. Also, GpS can up-regulate the expression of p-GSK3β at Ser9, suggesting that GpS may activate the Wnt/β-catenin pathway through activation of the cAMP/PKA pathway to mediate melanogenesis (FIG. 14).

The major active components of the aerial parts of Gp are a series of dammarane-type saponins. These include eight gypenosides structurally identical to the known ginsenosides Rd, Rb1, Rb3, F2, Rc and Rg3, and malonylginsenosides Rb1 and Rd that were initially isolated from ginseng. The total GpS is separated by chromatography to obtain the fractions of GpS, Fr.1 to Fr.10. GpS fractions 5-9 significantly induce both tyrosinase activity and melanin synthesis in B16 cells. The GpS fractions' involvement in the expression of melanogenic molecules are then investigated. According to the results of tyrosinase activity and melanin content, only GpS Fr. 7 induces all the expressions of melanogenic molecules. Furthermore, only GpS Fr.7 significantly induces both β-catenin and p-CREB. In conclusion, although the GpS fractions 5-9 stimulate the melanin production, there are no simultaneous induced expressions of all melanogenic proteins, like Fr.7, it significantly activate the tyrosinase activity and melanin content, also up-regulating the expressions of TRPs and tyrosinase, however, down-regulating the expression of MITF.

CONCLUSION

The present invention provides a composition comprising GpS for inducing tyrosinase activity, melanin synthesis, and up-regulating the protein expressions of melanogenic molecules, p-CREB, p-GSK3β (Ser9) and β-catenin. The present invention also provides GpS fractions for use in melanogenesis.

INDUSTRIAL APPLICABILITY

The present invention discloses saponins fractions isolated from natural sources for its therapeutic uses in melanin production. More particularly, it relates to saponins fractions extracted from *Gynostemma Pentaphyllum* and their melanogenesis effects.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What is claimed is:

1. A method for inducing melanogenesis in cells comprising administering a composition comprising an effective amount of saponins extracted from *Gynostemma* species to said cells at a non-acidic pH, wherein the effective amount is 50-150 μg/ml saponins extracted from *Gynostemma* species.

2. The method according to claim 1 wherein the *Gynostemma* species comprises *Gynostemma pentaphyllum*.

3. The method according to claim 1 wherein the saponins are extracted from the aerial part of *Gynostemma* species.

4. The method according to claim 1, wherein the composition further comprises one or more fractions of said saponins being characterized to induce tyrosinase activity, melanin synthesis, and up-regulate protein expressions of melanogenic molecules.

5. The method according to claim 1 wherein the cells comprises cells from human.

6. The method according to claim 1, wherein the pH is substantially neutral.

7. The method according to claim 1, wherein the pH is 7.4.

* * * * *